(12) United States Patent
Yoo et al.

(10) Patent No.: US 11,723,984 B2
(45) Date of Patent: Aug. 15, 2023

(54) METHOD FOR CONJUGATING ANTIBODY AND PHYSIOLOGICALLY ACTIVE SUBSTANCE

(71) Applicant: NOVELTY NOBILITY INC., Seongnam-si (KR)

(72) Inventors: Tae Hyeon Yoo, Yongin-si (KR); Jisoo Park, Suwon-si (KR); Yumi Lee, Suwon-si (KR)

(73) Assignee: NOVELTY NOBILITY INC., Seongnam-si (KR)

( * ) Notice: Subject to any disclaimer, the term of this patent is extended or adjusted under 35 U.S.C. 154(b) by 362 days.

(21) Appl. No.: 16/768,331

(22) PCT Filed: Nov. 29, 2018

(86) PCT No.: PCT/KR2018/014939
§ 371 (c)(1),
(2) Date: May 29, 2020

(87) PCT Pub. No.: WO2019/107962
PCT Pub. Date: Jun. 6, 2019

(65) Prior Publication Data
US 2020/0397912 A1    Dec. 24, 2020

(30) Foreign Application Priority Data

Nov. 29, 2017  (KR) .......................... 10-2017-0161452
Nov. 23, 2018  (KR) .......................... 10-2018-0146289

(51) Int. Cl.
*A61K 47/68* (2017.01)
*A61K 47/65* (2017.01)
*C07K 7/08* (2006.01)

(52) U.S. Cl.
CPC .............. *A61K 47/68* (2017.08); *A61K 47/65* (2017.08); *C07K 7/08* (2013.01)

(58) Field of Classification Search
CPC ........ A61K 47/65; A61K 47/68; A61K 68/89; C07K 7/08
See application file for complete search history.

(56) References Cited

U.S. PATENT DOCUMENTS

| 9,388,222 B2 | 7/2016 | Pastan et al. |
| 2004/0253247 A1 | 12/2004 | Dennis et al. |
| 2016/0041157 A1 | 2/2016 | Tsourkas et al. |

FOREIGN PATENT DOCUMENTS

| JP | 2003-518075 A | 6/2003 |
| KR | 10-2009-0117406 A | 11/2009 |
| KR | 10-2014-0004530 A | 1/2014 |
| KR | 10-1695684 B1 | 1/2017 |
| WO | 2008/044038 A2 | 4/2008 |
| WO | 2014/145654 A1 | 9/2014 |

OTHER PUBLICATIONS

Yongwon Jung et al., "Photoactivable Antibody Binding Protein Site-Selective and Covalent Coupling of Antibody", Anal. Chem. 2009, pp. 936-942, vol. 81, No. 3.
Yoshihito Tanaka et al., "Photocrosslinkers illuminate interactions in living cells", Molecular BioSystems, 2008, pp. 473-480, vol. 4, No. 6.
Warren L. DeLano et al., "Convergent Solutions to Binding at a Protein-Protein Interface", Science, Feb. 18, 2000, pp. 1279-1283, vol. 287.
Jason W. Chin et al., "Addition of a photocrosslinking amino acid to the genetic code of *Escherichia coli*", Aug. 20, 2002, pp. 11020-11024, vol. 99, No. 17.
Byeong Sung Lee et al., "An efficient system for incorporation of unnatural amino acids in response to the four-base codon AGGA in *Escherichia coli*", Biochimica Biophysica Acta, S0304-4165, 2017.
Korean Office Action of KR 10-2018-0146289 dated Jul. 2, 2019.
International Search Report for PCT/KR2018/014939 dated May 21, 2019 [PCT/ISA/210].
Jisoo Park et al., "Peptide-Directed Photo-Cross-Linking for Site-Specific Conjugation of IgG", Bioconjugate Chemistry, Sep. 4, 2018, vol. 29, pp. 3240-3244 (5 pages total).
Anna Konrad et al., "Covalent Immunoglobulin Labeling through a Photoactivable Synthetic Z Domain", Bioconjugate Chemistry, Oct. 26, 2011, vol. 22, pp. 2395-2403 (9 pages total).
Extended European Search Report dated Jul. 16, 2021 in European Application No. 18882347.0.
Office Action dated Jun. 15, 2021 in Japanese Application No. 2020-549533.

*Primary Examiner* — James W Rogers
(74) *Attorney, Agent, or Firm* — Sughrue Mion, PLLC

(57) ABSTRACT

The present invention relates to an antibody conjugating peptide including an amino acid having a photoreactive functional group, a physiologically active substance modified with the conjugating peptide, and an antibody conjugate having an antibody linked to the physiologically active substance. When the physiologically active substance modified with the conjugating peptide according to the present invention is linked to the antibody, the conjugation efficiency between the antibody and the physiologically active substance is remarkably improved as compared to that of the conventional art, and thus, the drug may be firmly bound without impairing the specificity of the antibody, thereby making it possible to accelerate commercialization of the antibody conjugate.

1 Claim, 16 Drawing Sheets
Specification includes a Sequence Listing.

□: trastuzumab
△: PE24
○: trastuzumab-PE24.

(A) Her2-positive/trastuzumab-sensitive
(B) Her2-positive/trastuzumab-resistant
(C) Her2-positive/trastuzumab-resistant
(D) Her2-negative

SEQUENCE LISTING

```
<160> NUMBER OF SEQ ID NOS: 29

<210> SEQ ID NO 1
<211> LENGTH: 13
<212> TYPE: PRT
<213> ORGANISM: Artificial Sequence
<220> FEATURE:
<223> OTHER INFORMATION: FcIII

<400> SEQUENCE: 1

Asp Cys Ala Trp His Leu Gly Glu Leu Val Trp Cys Thr
1               5                   10

<210> SEQ ID NO 2
<211> LENGTH: 39
<212> TYPE: DNA
<213> ORGANISM: Artificial Sequence
<220> FEATURE:
<223> OTHER INFORMATION: FcIII

<400> SEQUENCE: 2
gattgtgcat ggcatttagg tgaattagtg tggtgtaca                              39

<210> SEQ ID NO 3
<211> LENGTH: 241
<212> TYPE: PRT
<213> ORGANISM: Artificial Sequence
<220> FEATURE:
<223> OTHER INFORMATION: beta-lactamase

<400> SEQUENCE: 3
```

```
Glu Thr Leu Val Lys Val Lys Asp Ala Glu Asp Gln Leu Gly Ala Arg
1               5                   10                  15

Val Gly Tyr Ile Glu Leu Asp Leu Asn Ser Gly Lys Ile Leu Glu Ser
            20                  25                  30

Phe Arg Pro Glu Glu Arg Phe Pro Met Met Ser Thr Phe Lys Val Leu
        35                  40                  45

Leu Cys Gly Ala Val Leu Ser Arg Ile Asp Ala Gly Gln Glu Gln Leu
    50                  55                  60

Gly Arg Arg Ile His Tyr Ser Gln Asn Asp Leu Val Glu Tyr Ser Pro
65                  70                  75                  80

Val Thr Glu Lys His Leu Thr Asp Gly Met Thr Val Arg Glu Leu Cys
                85                  90                  95

Ser Ala Ala Ile Thr Met Ser Asp Asn Thr Ala Ala Asn Leu Leu Leu
                100                 105                 110

Thr Thr Ile Gly Gly Pro Lys Glu Leu Thr Ala Phe Leu His Asn Met
            115                 120                 125

Gly Asp His Val Thr Arg Leu Asp Arg Trp Glu Pro Glu Leu Asn Glu
130                 135                 140

Ala Ile Pro Asn Asp Glu Arg Asp Thr Thr Met Pro Ala Ala Met Ala
145                 150                 155                 160

Thr Thr Leu Arg Lys Leu Leu Thr Gly Glu Leu Leu Thr Leu Ala Ser
                165                 170                 175

Arg Gln Gln Leu Ile Asp Trp Met Glu Ala Asp Lys Val Ala Gly Pro
            180                 185                 190

Leu Leu Arg Ser Ala Leu Pro Ala Gly Trp Phe Ile Ala Asp Lys Ser
        195                 200                 205

Gly Ala Gly Glu Arg Gly Ser Arg Gly Ile Ile Ala Ala Leu Gly Pro
    210                 215                 220

Asp Gly Lys Pro Ser Arg Ile Val Val Ile Tyr Thr Thr Gly Ser Gln
225                 230                 235                 240

Ala
```

<210> SEQ ID NO 4
<211> LENGTH: 723
<212> TYPE: DNA
<213> ORGANISM: Artificial Sequence
<220> FEATURE:
<223> OTHER INFORMATION: beta-lactamase

<400> SEQUENCE: 4

```
gaaacgctgg tgaaagtaaa agatgctgaa gatcagttgg gtgcacgagt gggttacatc      60
gaactggatc tcaacagcgg taagatcctt gagagttttc gccccgaaga acgttttcca     120
atgatgagca cttttaaagt tctgctatgt ggcgcggtat tatcccgtat tgacgccggg     180
caagagcaac tcggtcgccg catacactat tctcagaatg acttggttga gtactcacca     240
gtcacagaaa agcatcttac ggatggcatg acagtaagag aattatgcag tgctgccata     300
accatgagtg ataacactgc ggccaactta cttctgacaa cgatcggagg accgaaggag     360
ctaaccgctt ttttgcacaa catgggggat catgtaactc gccttgatcg ttgggaaccg     420
gagctgaatg aagccatacc aaacgacgag cgtgacacca cgatgcctgc agcaatggca     480
acaacgttgc gcaaactatt aactggcgaa ctacttactc tagcttcccg gcaacaatta     540
atagactgga tggaggcgga taaagttgca ggaccacttc tgcgctcggc ccttccggct     600
ggctggttta ttgctgataa atctggagcc ggtgagcgtg gtctcgcgg tatcattgca     660
```

-continued

```
gcactggggc cagatggtaa gccctcccgt atcgtagtta tctacacgac ggggagtcag      720
gca                                                                   723
```

<210> SEQ ID NO 5
<211> LENGTH: 452
<212> TYPE: PRT
<213> ORGANISM: Artificial Sequence
<220> FEATURE:
<223> OTHER INFORMATION: beta-lactamase zymogen

<400> SEQUENCE: 5

```
Gly Gly Ala Gly Val Met Thr Gly Ala Lys Phe Thr Gln Ile Gln Phe
1               5                   10                  15

Gly Met Thr Arg Gln Gln Val Leu Asp Ile Ala Gly Ala Glu Asn Cys
            20                  25                  30

Glu Thr Gly Gly Ser Phe Gly Asp Ser Ile His Cys Arg Gly His Ala
        35                  40                  45

Ala Gly Asp Tyr Tyr Ala Tyr Ala Thr Phe Gly Phe Thr Ser Ala Ala
    50                  55                  60

Ala Asp Ala Lys Val Asp Ser Lys Ser Gln Glu Lys Leu Leu Ala Pro
65                  70                  75                  80

Ser Ala Pro Thr Leu Thr Leu Ala Lys Phe Asn Gln Val Thr Val Gly
                85                  90                  95

Met Thr Arg Ala Gln Val Leu Ala Thr Val Gly Gln Gly Ser Cys Thr
            100                 105                 110

Thr Trp Ser Glu Tyr Tyr Pro Ala Tyr Pro Ser Thr Ala Gly Val Thr
        115                 120                 125

Leu Ser Leu Ser Cys Phe Asp Val Asp Gly Tyr Ser Ser Thr Gly Ala
    130                 135                 140

Tyr Arg Gly Ser Ala His Leu Trp Phe Thr Asp Gly Val Leu Gln Gly
145                 150                 155                 160

Lys Arg Gln Trp Asp Leu Val Gly Ser Gly Gly Ser Gly Pro Leu
                165                 170                 175

Gly Val Arg Gly Gly Gly Ser Lys Leu Met Asp Glu Arg Asn Arg Gln
            180                 185                 190

Ile Ala Glu Ile Gly Ala Ser Leu Ile Lys His Trp Gly Gly Gly
        195                 200                 205

Gly His Pro Glu Thr Leu Val Lys Val Lys Asp Ala Glu Asp Gln Leu
    210                 215                 220

Gly Ala Arg Val Gly Tyr Ile Glu Leu Asp Leu Asn Ser Gly Lys Ile
225                 230                 235                 240

Leu Glu Ser Phe Arg Pro Glu Glu Arg Phe Pro Met Met Ser Thr Phe
                245                 250                 255

Lys Val Leu Leu Cys Gly Ala Val Leu Ser Arg Ile Asp Ala Gly Gln
            260                 265                 270

Glu Gln Leu Gly Arg Arg Ile His Tyr Ser Gln Asn Asp Leu Val Glu
        275                 280                 285

Tyr Ser Pro Val Thr Glu Lys His Leu Thr Asp Gly Met Thr Val Arg
    290                 295                 300

Glu Leu Cys Ser Ala Ala Ile Thr Met Ser Asp Asn Thr Ala Ala Asn
305                 310                 315                 320

Leu Leu Leu Thr Thr Ile Gly Gly Pro Lys Glu Leu Thr Ala Phe Leu
                325                 330                 335

His Asn Met Gly Asp His Val Thr Arg Leu Asp Arg Trp Glu Pro Glu
            340                 345                 350
```

```
Leu Asn Glu Ala Ile Pro Asn Asp Glu Arg Asp Thr Thr Thr Pro Val
            355                 360                 365

Ala Met Ala Thr Thr Leu Arg Lys Leu Leu Thr Gly Glu Leu Leu Thr
    370                 375                 380

Leu Ala Ser Arg Gln Gln Leu Ile Asp Trp Met Glu Ala Asp Lys Val
385                 390                 395                 400

Ala Gly Pro Leu Leu Arg Ser Ala Leu Pro Ala Gly Trp Phe Ile Ala
                405                 410                 415

Asp Lys Ser Gly Ala Gly Glu Arg Gly Ser Arg Gly Ile Ile Ala Ala
                420                 425                 430

Leu Gly Pro Asp Gly Glu Pro Ser Arg Ile Val Val Ile Tyr Thr Thr
                435                 440                 445

Gly Ser Gln Ala
        450

<210> SEQ ID NO 6
<211> LENGTH: 1356
<212> TYPE: DNA
<213> ORGANISM: Artificial Sequence
<220> FEATURE:
<223> OTHER INFORMATION: beta-lactamase zymogen

<400> SEQUENCE: 6
ggcggtgcgg gggtgatgac cggggcgaag ttcacgcaga tccagttcgg gatgacacgt      60
cagcaggtcc tcgacatagc cggtgcggag aactgtgaga ccggcgggtc gttcggggac     120 agcatcccact gccgggggca cgcggcaggg gactactacg cctacgccac cttcggcttc    180
accagcgccg ccgccgacgc gaaggtggac tcgaagagcc aggagaagct gctggccccg    240
agcgccccga cgctcaccct cgccaagttc aaccaggtca ccgtggggat gaccagggcc    300
caggtactgg cgaccgtcgg gcaggggtcc tgcaccacct ggagtgagta ctacccggcc    360
tatccgtcga cggccgggt gaccctcagc ctgtcctgct cgatgtgga cggttactcg     420 tcgacgggg cctaccgagg ctcggcgcac ctctggttca cggacggggt gcttcagggc     480
aagcggcagt gggaccttgt aggatccggt ggcggcagcg gccgctgggg cgtgcgtggc    540
ggtggcagca agcttatgga cgagcgtaac cgtcaaattg cggaaatcgg cgcatctctg    600
atcaaacact ggggtggcgg cggtggccac ccagaaacgc tggtgaaagt aaaagatgct    660
gaagatcagt ggggtgcacg agtgggttac atcgaactgg atctcaacag cggtaagatc    720
cttgagagtt ttcgccccga gaacgttttt ccaatgatga cactttttaa agttctgcta    780
tgtggcgcgg tattatcccg tattgacgcc gggcaagagc aactcggtcg ccgcatacac    840
tattctcaga tgacttggt tgagtactca ccagtcacag aaaagcatct acgatggc      900 atgacagtaa gagaattatg cagtgctgcc ataaccatga gtgataacac tgcggccaac    960
ttacttctga caacgatcgg aggaccgaag gagctaaccg cttttttgca caacatgggg   1020
gatcatgtaa ctcgccttga tcgttgggaa ccggagctga tgaagccat accaaacgac    1080 gagcgtgaca ccacgacgcc tgtagcaatg gcaacaacgt tgcgcaaact attaactggc    1140
gaactactta ctctagcttc ccggcaacaa ttgatagact ggatggaggc ggataaagtt   1200
gcaggaccac ttctgcgctc ggcccttccg gctggctggt ttattgctga taaatctgga    1260
gccggtgagc gtggctctcg cggtatcatt gcagcactgg ggccagatgg tgagccctcc    1320
cgtatcgtag ttatctacac gacggggagt caggca                             1356
```

<210> SEQ ID NO 7
<211> LENGTH: 233
<212> TYPE: PRT
<213> ORGANISM: Artificial Sequence
<220> FEATURE:
<223> OTHER INFORMATION: PE24

<400> SEQUENCE: 7

```
Arg His Arg Gln Pro Arg Gly Trp Glu Gln Leu Gly Gly Ser Pro Thr
1               5                   10                  15

Gly Ala Glu Phe Leu Gly Asp Gly Asp Val Ser Phe Ser Thr Arg
            20                  25                  30

Gly Thr Gln Asn Trp Thr Val Glu Arg Leu Leu Gln Ala His Ala Gln
        35                  40                  45

Leu Glu Glu Arg Gly Tyr Val Phe Val Gly Tyr His Gly Thr Phe Leu
    50                  55                  60

Glu Ala Ala Gln Ser Ile Val Phe Gly Gly Val Ala Ala Arg Ser Gln
65                  70                  75                  80

Asp Leu Ala Ala Ile Trp Ala Gly Phe Tyr Ile Ala Gly Asp Pro Ala
                85                  90                  95

Leu Ala Tyr Gly Tyr Ala Gln Asp Gln Glu Pro Asp Ala Ala Gly Arg
            100                 105                 110

Ile Arg Asn Gly Ala Leu Leu Arg Val Tyr Val Pro Ala Ser Ser Leu
        115                 120                 125

Pro Gly Phe Tyr Arg Thr Ser Leu Thr Leu Ala Ala Pro Glu Ala Ala
    130                 135                 140

Gly Glu Val Glu Arg Leu Ile Gly His Pro Leu Pro Leu Ala Leu Asp
145                 150                 155                 160

Ala Ile Thr Gly Pro Glu Glu Glu Gly Gly Arg Leu Glu Thr Ile Leu
                165                 170                 175

Gly Trp Pro Leu Ala Glu Arg Thr Val Val Ile Pro Ser Ala Ile Pro
            180                 185                 190

Thr Asp Pro Arg Asn Val Gly Gly Asp Leu Asp Pro Ser Ser Ile Pro
        195                 200                 205

Asp Lys Glu Gln Ala Ile Ser Ala Leu Pro Asp Tyr Ala Ser Gln Pro
    210                 215                 220

Gly Lys Pro Pro Arg Glu Asp Leu Lys
225                 230
```

<210> SEQ ID NO 8
<211> LENGTH: 699
<212> TYPE: DNA
<213> ORGANISM: Artificial Sequence
<220> FEATURE:
<223> OTHER INFORMATION: PE24

<400> SEQUENCE: 8

```
cgtcatcgtc agccgcgtgg ttgggaacag cttggtggtt cgcccactgg tgctgaattt      60
ctcggtgatg gtggtgacgt tagctttagc actcggggaa cccagaattg gacagttgaa     120
cgtttactgc aagctcatgc acagctggaa gaacgtggtt atgttttgt aggatatcat     180 ggtacattct tagaagcagc acaatctata gttttcggtg gtgtcgctgc gcgttcgcag     240
gatctggcag caatttgggc aggttttctat atcgcaggag atcctgctct tgcatacggt     300
tacgcacagg atcaggaacc agatgcagct ggtagaatcc gaaatggagc attgcttaga     360
gtgtatgttc cggcatcatc tctgcccggt ttttatagga cgagtctgac acttgcagca     420
ccagaagcag caggcgaagt tgaacgctta attggtcatc cgctgcctct cgcactggac     480
```

```
gcaatcactg gtccggaaga agaaggtggt cggctggaaa cgatactagg atggccgtta      540
gctgagcgta ccgtggtaat tccatccgcc ataccaaccg atccacgtaa cgtaggtggt      600
gatttagacc cgagcagtat tcccgataaa gaacaggcaa tctcagcatt gccggactac      660
gcttcacaac ctggtaaacc tcctcgtgaa gatctgaag                             699
```

<210> SEQ ID NO 9
<211> LENGTH: 306
<212> TYPE: PRT
<213> ORGANISM: Artificial Sequence
<220> FEATURE:
<223> OTHER INFORMATION: pBpa-aminoacyl tRNA synthetase
<400> SEQUENCE: 9

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 10
<211> LENGTH: 918
<212> TYPE: DNA
<213> ORGANISM: Artificial Sequence
<220> FEATURE:
<223> OTHER INFORMATION: pBpa-aminoacyl tRNA synthetase

<400> SEQUENCE: 10

```
atggacgagt tcgaaatgat taaacgcaac accagcgaaa ttatctctga agaagagctg      60
cgcgaggtgc tgaagaaaga cgagaagagc gcgggcattg gctttgagcc gtccggtaaa     120
attcacctgg gtcactacct gcaaatcaag aagatgattg atctgcaaaa cgctggtttt     180
gacatcatta tcctgctggc ggacctgcac gcctacctga tcaaaagggg cgagctggat     240
gagattcgca gatcggcga ctacaataag aaagtcttcg aagccatggg tttgaaggct     300
aaatacgtct acggtagcag ctttcagctg gataaggatt acacgttgaa tgtgtaccgt     360
ctggcgctga aaccacgct gaaacgcgcc cgtcgttcca tggagctgat tgcgcgcgag     420
gatgagaatc caaaagttgc tgaggttatt taccctatta tgcaagttaa taccagccac     480
tacctgggtg ttgatgttgc cgtcggtggt atggagcaac gcaaaattca catgctggca     540
cgtgaactgc tgccgaaaaa ggttgtctgt attcataatc cggtcctgac cggcctggat     600
ggcgagggta aaatgagcag cagcaagggt aactttattg cagttgacga tagcccggaa     660
gaaatccgtg cgaagatcaa gaaagcgtac tgcccggcag cgtggttga gggtaacccg     720
atcatggaaa tcgccaagta ttttctggaa tacccactga cgattaagcg cccggagaaa     780
tttggcggcg acctgaccgt caacagctac gaggagctgg aaagcttgtt taagaacaaa     840
gaactgcatc cgatgcgcct gaaaaacgcc gtggcggaag agctgattaa gattctggaa     900
ccaattcgca aacgtctg                                                   918
```

<210> SEQ ID NO 11
<211> LENGTH: 12
<212> TYPE: PRT
<213> ORGANISM: Artificial Sequence
<220> FEATURE:
<223> OTHER INFORMATION: H5amber FcIII

<400> SEQUENCE: 11

Asp Cys Ala Trp Leu Gly Glu Leu Val Trp Cys Thr
1               5                   10

<210> SEQ ID NO 12
<211> LENGTH: 39
<212> TYPE: DNA
<213> ORGANISM: Artificial Sequence
<220> FEATURE:
<223> OTHER INFORMATION: H5amber FcIII

<400> SEQUENCE: 12

```
gattgtgcat ggtagttagg tgaattagtg tggtgtaca                             39
```

<210> SEQ ID NO 13
<211> LENGTH: 12
<212> TYPE: PRT
<213> ORGANISM: Artificial Sequence
<220> FEATURE:
<223> OTHER INFORMATION: V10amber FcIII

<400> SEQUENCE: 13

Asp Cys Ala Trp His Leu Gly Glu Leu Trp Cys Thr
1               5                   10

<210> SEQ ID NO 14
<211> LENGTH: 39
<212> TYPE: DNA
<213> ORGANISM: Artificial Sequence
<220> FEATURE:
<223> OTHER INFORMATION: V10amber FcIII

<400> SEQUENCE: 14
gattgtgcat ggcatttagg tgaattatag tggtgtaca         39

<210> SEQ ID NO 15
<211> LENGTH: 12
<212> TYPE: PRT
<213> ORGANISM: Artificial Sequence
<220> FEATURE:
<223> OTHER INFORMATION: W11amber FcIII

<400> SEQUENCE: 15

Asp Cys Ala Trp His Leu Gly Glu Leu Val Cys Thr
1               5                  10

<210> SEQ ID NO 16
<211> LENGTH: 39
<212> TYPE: DNA
<213> ORGANISM: Artificial Sequence
<220> FEATURE:
<223> OTHER INFORMATION: W11amber FcIII

<400> SEQUENCE: 16
gattgtgcat ggcatttagg tgaattagtg tagtgtaca         39

<210> SEQ ID NO 17
<211> LENGTH: 271
<212> TYPE: PRT
<213> ORGANISM: Artificial Sequence
<220> FEATURE:
<223> OTHER INFORMATION: FcIII V10*-beta-lactamase

<400> SEQUENCE: 17

Asp Cys Ala Trp His Leu Gly Glu Leu Trp Cys Thr Gly Gly Glu Phe
1               5                  10                  15

Gly Gly Gly Ser Gly Gly Gly Ser Gly Ser Gly Gly Gly Ser Glu Thr
            20                  25                  30

Leu Val Lys Val Lys Asp Ala Glu Asp Gln Leu Gly Ala Arg Val Gly
        35                  40                  45

Tyr Ile Glu Leu Asp Leu Asn Ser Gly Lys Ile Leu Glu Ser Phe Arg
    50                  55                  60

Pro Glu Glu Arg Phe Pro Met Met Ser Thr Phe Lys Val Leu Leu Cys
65                  70                  75                  80

Gly Ala Val Leu Ser Arg Ile Asp Ala Gly Gln Glu Gln Leu Gly Arg
                85                  90                  95

Arg Ile His Tyr Ser Gln Asn Asp Leu Val Glu Tyr Ser Pro Val Thr
            100                 105                 110

Glu Lys His Leu Thr Asp Gly Met Thr Val Arg Glu Leu Cys Ser Ala
        115                 120                 125

Ala Ile Thr Met Ser Asp Asn Thr Ala Ala Asn Leu Leu Leu Thr Thr
    130                 135                 140

Ile Gly Gly Pro Lys Glu Leu Thr Ala Phe Leu His Asn Met Gly Asp
145                 150                 155                 160

His Val Thr Arg Leu Asp Arg Trp Glu Pro Glu Leu Asn Glu Ala Ile

```
             165                 170                 175
Pro Asn Asp Glu Arg Asp Thr Thr Met Pro Ala Ala Met Ala Thr Thr
            180                 185                 190

Leu Arg Lys Leu Leu Thr Gly Glu Leu Leu Thr Leu Ala Ser Arg Gln
        195                 200                 205

Gln Leu Ile Asp Trp Met Glu Ala Asp Lys Val Ala Gly Pro Leu Leu
    210                 215                 220

Arg Ser Ala Leu Pro Ala Gly Trp Phe Ile Ala Asp Lys Ser Gly Ala
225                 230                 235                 240

Gly Glu Arg Gly Ser Arg Gly Ile Ile Ala Leu Gly Pro Asp Gly
                245                 250                 255

Lys Pro Ser Arg Ile Val Val Ile Tyr Thr Thr Gly Ser Gln Ala
        260                 265                 270
```

<210> SEQ ID NO 18
<211> LENGTH: 819
<212> TYPE: DNA
<213> ORGANISM: Artificial Sequence
<220> FEATURE:
<223> OTHER INFORMATION: FcIII V10*-beta-lactamase

<400> SEQUENCE: 18

```
gattgtgcat ggcatttagg tgaattatag tggtgtacag gtggtgaatt cggtggtggt      60
tcaggaggtg gttcaggatc cggcggtggc agcgaaacgc tggtgaaagt aaaagatgct     120
gaagatcagt tgggtgcacg agtgggttac atcgaactgg atctcaacag cggtaagatc     180
cttgagagtt ttcgccccga agaacgtttt ccaatgatga gcactttttaa agttctgcta     240
tgtggcgcgg tattatcccg tattgacgcc gggcaagagc aactcggtcg ccgcatacac     300
tattctcaga tgacttggt tgagtactca ccagtcacag aaaagcatct tacgatggc      360
atgacagtaa gagaattatg cagtgctgcc ataaccatga gtgataacac tgcggccaac     420
ttacttctga caacgatcgg aggaccgaag gagctaaccg cttttttgca caacatgggg     480
gatcatgtaa ctcgccttga tcgttgggaa ccggagctga tgaagccat accaaacgac      540
gagcgtgaca ccacgatgcc tgcagcaatg gcaacaacgt tgcgcaaact attaactggc     600
gaactactta ctctagcttc ccggcaacaa ttaatagact ggatggaggc ggataaagtt     660
gcaggaccac ttctgcgctc ggcccttccg gctggctggt ttattgctga taaatctgga     720
gccggtgagc gtgggtctcg cggtatcatt gcagcactgg gccagatgg taagccctcc      780
cgtatcgtag ttatctacac gacggggagt caggcataa                            819
```

<210> SEQ ID NO 19
<211> LENGTH: 466
<212> TYPE: PRT
<213> ORGANISM: Artificial Sequence
<220> FEATURE:
<223> OTHER INFORMATION: FcIII V10*-beta-lactamase zymogen

<400> SEQUENCE: 19

```
Asp Cys Ala Trp His Leu Gly Glu Leu Trp Cys Thr Pro Trp Gly Gly
1               5                   10                  15

Met Asp Glu Arg Asn Arg Gln Ile Ala Glu Ile Gly Ala Ser Leu Ile
            20                  25                  30

Lys His Trp Gly Gly Gly Gly His Pro Glu Thr Leu Val Lys Val
        35                  40                  45

Lys Asp Ala Glu Asp Gln Leu Gly Ala Arg Val Gly Tyr Ile Glu Leu
    50                  55                  60
```

```
Asp Leu Asn Ser Gly Lys Ile Leu Glu Ser Phe Arg Pro Glu Glu Arg
 65                  70                  75                  80

Phe Pro Met Met Ser Thr Phe Lys Val Leu Leu Cys Gly Ala Val Leu
                 85                  90                  95

Ser Arg Ile Asp Ala Gly Gln Glu Gln Leu Gly Arg Arg Ile His Tyr
            100                 105                 110

Ser Gln Asn Asp Leu Val Glu Tyr Ser Pro Val Thr Glu Lys His Leu
        115                 120                 125

Thr Asp Gly Met Thr Val Arg Glu Leu Cys Ser Ala Ala Ile Thr Met
    130                 135                 140

Ser Asp Asn Thr Ala Ala Asn Leu Leu Leu Thr Thr Ile Gly Gly Pro
145                 150                 155                 160

Lys Glu Leu Thr Ala Phe Leu His Asn Met Gly Asp His Val Thr Arg
                165                 170                 175

Leu Asp Arg Trp Glu Pro Glu Leu Asn Glu Ala Ile Pro Asn Asp Glu
            180                 185                 190

Arg Asp Thr Thr Thr Pro Val Ala Met Ala Thr Thr Leu Arg Lys Leu
        195                 200                 205

Leu Thr Gly Glu Leu Leu Thr Leu Ala Ser Arg Gln Gln Leu Ile Asp
    210                 215                 220

Trp Met Glu Ala Asp Lys Val Ala Gly Pro Leu Leu Arg Ser Ala Leu
225                 230                 235                 240

Pro Ala Gly Trp Phe Ile Ala Asp Lys Ser Gly Ala Gly Glu Arg Gly
                245                 250                 255

Ser Arg Gly Ile Ile Ala Ala Leu Gly Pro Asp Gly Glu Pro Ser Arg
            260                 265                 270

Ile Val Val Ile Tyr Thr Thr Gly Ser Gln Ala Gly Ser Gly Gly Gly
        275                 280                 285

Ser Gly Pro Leu Gly Val Arg Gly Gly Ser Lys Leu Ala Gly Val
    290                 295                 300

Met Thr Gly Ala Lys Phe Thr Gln Ile Gln Phe Gly Met Thr Arg Gln
305                 310                 315                 320

Gln Val Leu Asp Ile Ala Gly Ala Glu Asn Cys Glu Thr Gly Gly Ser
                325                 330                 335

Phe Gly Asp Ser Ile His Cys Arg Gly His Ala Ala Gly Asp Tyr Tyr
            340                 345                 350

Ala Tyr Ala Thr Phe Gly Phe Thr Ser Ala Ala Asp Ala Lys Val
        355                 360                 365

Asp Ser Lys Ser Gln Glu Lys Leu Leu Ala Pro Ser Ala Pro Thr Leu
    370                 375                 380

Thr Leu Ala Lys Phe Asn Gln Val Thr Val Gly Met Thr Arg Ala Gln
385                 390                 395                 400

Val Leu Ala Thr Val Gly Gln Gly Ser Cys Thr Thr Trp Ser Glu Tyr
                405                 410                 415

Tyr Pro Ala Tyr Pro Ser Thr Ala Gly Val Thr Leu Ser Leu Ser Cys
            420                 425                 430

Phe Asp Val Asp Gly Tyr Ser Ser Thr Gly Phe Tyr Arg Gly Ser Ala
        435                 440                 445

His Leu Trp Phe Thr Asp Gly Val Leu Gln Gly Lys Arg Gln Trp Asp
    450                 455                 460

Leu Val
465
```

<210> SEQ ID NO 20
<211> LENGTH: 1404
<212> TYPE: DNA
<213> ORGANISM: Artificial Sequence
<220> FEATURE:
<223> OTHER INFORMATION: FcIII V10*-beta-lactamase zymogen

<400> SEQUENCE: 20

```
gattgtgcat ggcatttagg tgaattatag tggtgtacac catggggcgg tatggacgag      60
cgtaaccgtc aaattgcgga atcggcgca tctctgatca acactgggg tggcggcggt       120
ggccacccag aaacgctggt gaaagtaaaa gatgctgaag atcagttggg tgcacgagtg     180
ggttacatcg aactggatct caacagcggt aagatccttg agagttttcg ccccgaagaa     240
cgttttccaa tgatgagcac ttttaaagtt ctgctatgtg cgcgggtatt atcccgtatt     300
gacgccgggc aagagcaact cggtcgccgc atacactatt ctcagaatga cttggttgag   360
tactcaccag tcacagaaaa gcatcttacg gatggcatga cagtaagaga attatgcagt    420
gctgccataa ccatgagtga taacactgcg gccaacttac ttctgacaac gatcggagga    480
ccgaaggagc taaccgcttt tttgcacaac atggggatc atgtaactcg ccttgatcgt     540
tgggaaccgg agctgaatga agccatacca acgacgagc gtgacaccac gacgcctgta    600
gcaatggcaa caacgttgcg caaactatta actggcgaac tacttactct agcttcccgg    660
caacaattga tagactggat ggaggcggat aaagttgcag gaccacttct cgctcggcc     720
cttccggctg gctggtttat tgctgataaa tctggagccg gtgagcgtgg ctctcgcggt     780
atcattgcag cactggggcc agatggtgag ccctcccgta tcgtagttat ctacacgacg    840
gggagtcagg caggatccgg tggcggcagc ggcccgctgg gcgtgcgtgg cggtggcagc    900
aagcttgcgg gggtgatgac cggggcgaag ttcacgcaga tccagttcgg gatgacacgt    960
cagcaggtcc tcgacatagc cggtgcggag aactgtgaga ccggcgggtc gttcggggac   1020
agcatccact gccgggggca cgcggcaggg gactactacg cctacgccac cttcggcttc   1080
accagcgccg ccgccgacgc gaaggtggac tcgaagagcc aggagaagct gctggccccg   1140
agcgccccga cgctcacccct cgccaagttc aaccaggtca ccgtggggat gaccagggcc   1200
caggtactgg cgaccgtcgg gcaggggtcc tgcaccacct ggagtgagta ctacccggcc    1260
tatccgtcga cggccgggt gaccctcagc ctgtcctgct cgatgtgga cggttactcg      1320
tcgacggggt tctaccgagg ctcggcgcac ctctggttca cggacggggt gcttcagggc   1380
aagcggcagt gggaccttgt ataa                                            1404
```

<210> SEQ ID NO 21
<211> LENGTH: 259
<212> TYPE: PRT
<213> ORGANISM: Artificial Sequence
<220> FEATURE:
<223> OTHER INFORMATION: FcIII V10*-PE24

<400> SEQUENCE: 21

Asp Cys Ala Trp His Leu Gly Glu Leu Trp Cys Thr Gly Gly Glu Phe
1               5                   10                  15

Gly Gly Gly Ser Gly Gly Gly Ser Gly Ser Arg His Arg Gln Pro Arg
            20                  25                  30

Gly Trp Glu Gln Leu Gly Gly Ser Pro Thr Gly Ala Glu Phe Leu Gly
        35                  40                  45

Asp Gly Gly Asp Val Ser Phe Ser Thr Arg Gly Thr Gln Asn Trp Thr
    50                  55                  60

```
Val Glu Arg Leu Leu Gln Ala His Ala Gln Leu Glu Arg Gly Tyr
 65                  70                  75                  80

Val Phe Val Gly Tyr His Gly Thr Phe Leu Glu Ala Ala Gln Ser Ile
                 85                  90                  95

Val Phe Gly Gly Val Ala Ala Arg Ser Gln Asp Leu Ala Ala Ile Trp
            100                 105                 110

Ala Gly Phe Tyr Ile Ala Gly Asp Pro Ala Leu Ala Tyr Gly Tyr Ala
            115                 120                 125

Gln Asp Gln Glu Pro Asp Ala Ala Gly Arg Ile Arg Asn Gly Ala Leu
130                 135                 140

Leu Arg Val Tyr Val Pro Ala Ser Ser Leu Pro Gly Phe Tyr Arg Thr
145                 150                 155                 160

Ser Leu Thr Leu Ala Ala Pro Glu Ala Ala Gly Glu Val Glu Arg Leu
                165                 170                 175

Ile Gly His Pro Leu Pro Leu Ala Leu Asp Ala Ile Thr Gly Pro Glu
            180                 185                 190

Glu Glu Gly Gly Arg Leu Glu Thr Ile Leu Gly Trp Pro Leu Ala Glu
            195                 200                 205

Arg Thr Val Val Ile Pro Ser Ala Ile Pro Thr Asp Pro Arg Asn Val
210                 215                 220

Gly Gly Asp Leu Asp Pro Ser Ser Ile Pro Asp Lys Glu Gln Ala Ile
225                 230                 235                 240

Ser Ala Leu Pro Asp Tyr Ala Ser Gln Pro Gly Lys Pro Pro Arg Glu
                245                 250                 255

Asp Leu Lys

<210> SEQ ID NO 22
<211> LENGTH: 929
<212> TYPE: DNA
<213> ORGANISM: Artificial Sequence
<220> FEATURE:
<223> OTHER INFORMATION: FcIII V10*-PE24

<400> SEQUENCE: 22
catatgaaaa aaaccgcaat tgcgattgca gttgcattgg ctggttttgc aacggtggca      60
caagcagcta gccatcatca tcaccatcac ggcagtttag ttccgcgtgg cagcggtggt     120
ggaagtaagc ttggaggtga ttgtgcatgg catttaggtg aattatagtg gtgtacaggt     180
ggtgaattcg gtggtggttc aggaggtggt tcaggatccc gtcatcgtca gccgcgtggt     240
tgggaacagc ttggtggttc gcccactggt gctgaatttc tcggtgatgg tgtgacgtt      300 agctttagca ctcggggaac ccagaattgg acagttgaac gtttactgca agctcatgca     360
cagctggaag aacgtggtta tgtttttgta ggatatcatg gtacattctt agaagcagca     420
caatctatag ttttcggtgg tgtcgctgcg cgttcgcagg atctggcagc aatttgggca     480
ggtttctata tcgcaggaga tcctgctctt gcatacggtt acgcacagga tcaggaacca     540
gatgcagctg gtagaatccg aaatggagca ttgcttagag tgtatgttcc ggcatcatct     600
ctgcccggtt tttataggac gagtctgaca cttgcagcac cagaagcagc aggcgaagtt     660
gaacgcttaa ttggtcatcc gctgcctctc gcactggacg caatcactgg tccgaagaa      720 gaaggtggtc ggctggaaac gatactagga tggccgttag ctgagcgtac cgtggtaatt     780
ccatccgcca taccaaccga tccacgtaac gtaggtggtg atttagaccc gagcagtatt     840
cccgataaag aacaggcaat ctcagcattg ccggactacg cttcacaacc tggtaaacct     900
```
cctcgtgaag atctgaagta agcggccgc                                             929

<210> SEQ ID NO 23
<211> LENGTH: 77
<212> TYPE: RNA
<213> ORGANISM: Artificial Sequence
<220> FEATURE:
<223> OTHER INFORMATION: tRNACUA

<400> SEQUENCE: 23
cccgccuuag uucagcaggg cagaacggcg gacucuaaau ccgcauggca cgdguucaaa          60
ucccguaggc gggacca                                                         77

<210> SEQ ID NO 24
<211> LENGTH: 49
<212> TYPE: DNA
<213> ORGANISM: Artificial Sequence
<220> FEATURE:
<223> OTHER INFORMATION: BamhI- -f primer

<400> SEQUENCE: 24
aaccttggat ccggcggtgg cagcgaaacg ctggtgaaag taaaagatg                      49

<210> SEQ ID NO 25
<211> LENGTH: 39
<212> TYPE: DNA
<213> ORGANISM: Artificial Sequence
<220> FEATURE:
<223> OTHER INFORMATION: TEM1-NotI-r primer

<400> SEQUENCE: 25
aaggttgcgg ccgctttatt accaatgctt aatcagtga                                 39

<210> SEQ ID NO 26
<211> LENGTH: 34
<212> TYPE: DNA
<213> ORGANISM: Artificial Sequence
<220> FEATURE:
<223> OTHER INFORMATION: Nde1-FcIII V10*-f primer

<400> SEQUENCE: 26
aaccttcata tgaagaaaac agcaattgct attg                                      34

<210> SEQ ID NO 27
<211> LENGTH: 33
<212> TYPE: DNA
<213> ORGANISM: Artificial Sequence
<220> FEATURE:
<223> OTHER INFORMATION: FcIII V10*-NcoI -r primer

<400> SEQUENCE: 27
aaggttccat ggtgtacacc actataattc acc                                       33

<210> SEQ ID NO 28
<211> LENGTH: 40
<212> TYPE: DNA
<213> ORGANISM: Artificial Sequence
<220> FEATURE:
<223> OTHER INFORMATION: NcoI -beta-lactamase zymogen -f primer

<400> SEQUENCE: 28
aaccttccat ggggcggtat ggacgagcgt aaccgtcaaa                                40

<210> SEQ ID NO 29
<211> LENGTH: 40

```
<212> TYPE: DNA
<213> ORGANISM: Artificial Sequence
<220> FEATURE:
<223> OTHER INFORMATION: beta-lactamase zymogen-NotI-r primer

<400> SEQUENCE: 29
aaggttgcgg ccgctttata caaggtccca ctgccgcttg                40
```

METHOD FOR CONJUGATING ANTIBODY AND PHYSIOLOGICALLY ACTIVE SUBSTANCE

CROSS REFERENCE TO RELATED APPLICATIONS

This application is a National Stage of International Application No. PCT/KR2018/014939 filed Nov. 29, 2018, claiming priority based on Korean Patent Application No. 10-2017-0161452 filed Nov. 29, 2017 and Korean Patent Application No. 10-2018-0146289 filed Nov. 23, 2018.

TECHNICAL FIELD

The present invention relates to an Fc site-specific conjugating peptide in which position 5, 10, or 11 of an Fc binding peptide represented by an amino acid sequence of SEQ ID NO: 1 is substituted with an amino acid having a photoreactive functional group, a physiologically active substance modified with the conjugating peptide, an antibody conjugate in which an antibody is covalently linked to the physiologically active substance modified with the conjugating peptide, and a method of producing the antibody conjugate.

BACKGROUND ART

For the past 20 years, antibody engineering has advanced thanks to the development of techniques for producing chimeric antibodies (chimeric mAbs), humanized antibodies (humanized mAb), and fully human antibodies (fully human mAbs) on the basis of hybridoma technology for developing monoclonal antibodies (mAbs) in mice, and antibodies are now recognized as a therapeutic drug (therapeutic mAb). 28 types of therapeutic antibodies have been approved by the FDA to date, and are used as agents for treating a wide range of diseases, such as transplant rejection, cancer, autoimmune diseases, inflammation, heart disease, and infection, and about 300 therapeutic antibodies are currently in the clinical development stage, with more therapeutic antibodies expected to be developed and commercialized in the future. In addition, many studies are ongoing to develop next-generation therapeutic antibodies that have improved efficacy over conventional antibodies (naked mAb). Among these, conjugates, in which a monoclonal antibody having a binding affinity to a specific antigen and a substance having biological activity are linked, are actively researched. When these antibody conjugates are developed as therapeutic drugs, the high efficacy and reduced side effects of the substance can be expected due to the target specificity of antibodies, and moreover, the characteristics of antibodies, such as no in-vivo toxicity, low immunogenicity, and long in-vivo half-life, are also factors that can accelerate the commercialization of developed antibody conjugate drugs. Antibody-drug conjugates (ADCs), in which an antibody and a small molecule drug exhibiting cytotoxicity are linked, have already been developed by pharmaceutical firms and are used as tumor-targeting therapeutic agents.

For development as a therapeutic drug, an antibody conjugate should retain the properties of an unconjugated antibody and the biologically active substance. The antibody conjugate must be able to maintain the same affinity as that of the (naked) antibody without conjugation to the substance. That is, natural antigen-antibody binding should not be hindered by linking an antibody with a substance. In addition, the substance in the antibody conjugate should also be able to exhibit activity after reaching a target. That is, in the antibody conjugate, the respective intrinsic properties of the monoclonal antibody and the biologically active substance must be maintained, which is determined by a method of conjugating the two molecules. In addition, linkers used for conjugation must be stable in the blood to prevent the substance from being separated from the antibody and to reach target tissues/cells. In general, linkers used in antibody conjugates are an acid-labile hydrazone, a protease-cleavable peptide, and a disulfide that is susceptible to a reducing agent. Non-cleavable thioether linkers are also used. For the conjugation of an antibody and a substance, a method using a reactive group (an ε-amino group of lysine or a thiol group of cysteine) of an antibody, or a method in which a cysteine residue is introduced into an antibody by a mutation and which uses the reactivity of the thiol group is generally used. The method using a functional group of an antibody itself cannot specify the position where a substance is linked, and the molar ratio of the antibody to the substance is not controllable, thus creating a heterogeneous antibody conjugate. In the case of using the thiol group of cysteine artificially introduced into an antibody, it is necessary to mutate the antibody, and it is difficult to predict the effect on the structure and activity of the antibody itself.

Recently, a method of producing a low-molecular-weight Fc conjugating peptides by introducing a photoreactive artificial amino acid into Fc binding peptides and then producing an antibody-drug conjugate using a drug modified with the Fc conjugating peptide (Korean Patent Publication No. 10-2014-0004530 (2014 Jan. 13)) have been reported. However, the peptide material used in the above inventions must be prepared through chemical synthesis, and thus, the conjugation method is limited to the case of conjugating a drug to an antibody, and it is difficult to use for the conjugation of a substance such as a protein and an antibody. In addition, the non-specific reactivity of the photoreactive amino acid (experimental example: using photo-leucine, photo-methionine) used in the above inventions makes it difficult to develop antibody conjugates as pharmaceuticals (Yoshihito Tanaka et al, *Molecular BioSystems*, 4(6):473-480, 2008).

Therefore, the inventors of the present invention developed an Fc site-specific conjugating peptide in which a site of an Fc binding peptide, which is capable of binding the Fc domain of an antibody, is substituted with an amino acid having a photoreactive functional group (para-benzoyl phenylalanine (pBpa)), and prepared a physiologically active substance modified with the conjugating peptide, and as a result of covalently linking the antibody and the substance through a reaction based on the introduced photoreactive amino acid, confirmed that the substance is conjugated to the antibody in a site-specific manner and with a high efficiency, thus completing the present invention.

The above information described in the Background Art section is provided only for the purpose of improving understanding of the background of the present invention, and thus may not include information that is already known to those of ordinary skill in the art to which the present invention pertains.

DISCLOSURE

Technical Problem

It is an object of the present invention to provide a peptide capable of site-specifically conjugating an antibody and a substance through photoreaction.

It is another object of the present invention to provide a substance modified with the peptide.

It is a further object of the present invention to provide a method of producing an antibody conjugate in which the substance modified with the peptide and an antibody are linked.

It is a further object of the present invention to provide an antibody conjugate produced using the production method.

Technical Solution

To achieve the above objects, the present invention provides an Fc site-specific conjugating peptide in which position 5, 10, or 11 in an Fc binding peptide represented by an amino acid sequence of SEQ ID NO: 1 is substituted with an amino acid having a photoreactive functional group.

The present invention also provides a substance modified with the conjugating peptide, wherein the substance is linked to the peptide either directly or via a linker.

The present invention also provides a method of producing an antibody conjugate, the method comprising: (a) mixing the substance modified with the conjugating peptide and an Fc domain-containing molecule; (b) irradiating the mixture with light to induce a photoreaction and then to produce an antibody conjugate in which the photoreactive functional group of the substance modified with the conjugating peptide and the Fc domain-containing molecule are covalently linked; and (c) obtaining the produced antibody conjugate.

The present invention also provides an antibody conjugate in which an antibody is linked to the substance modified with the conjugating peptide.

DETAILED DESCRIPTION AND EXEMPLARY EMBODIMENTS

Unless defined otherwise, all technical and scientific terms used herein have the same meanings as those commonly understood by one of ordinary skill in the art to which the present invention pertains. In general, the nomenclature used herein and experimental methods described below are well known and commonly used in the art.

Figure 1:
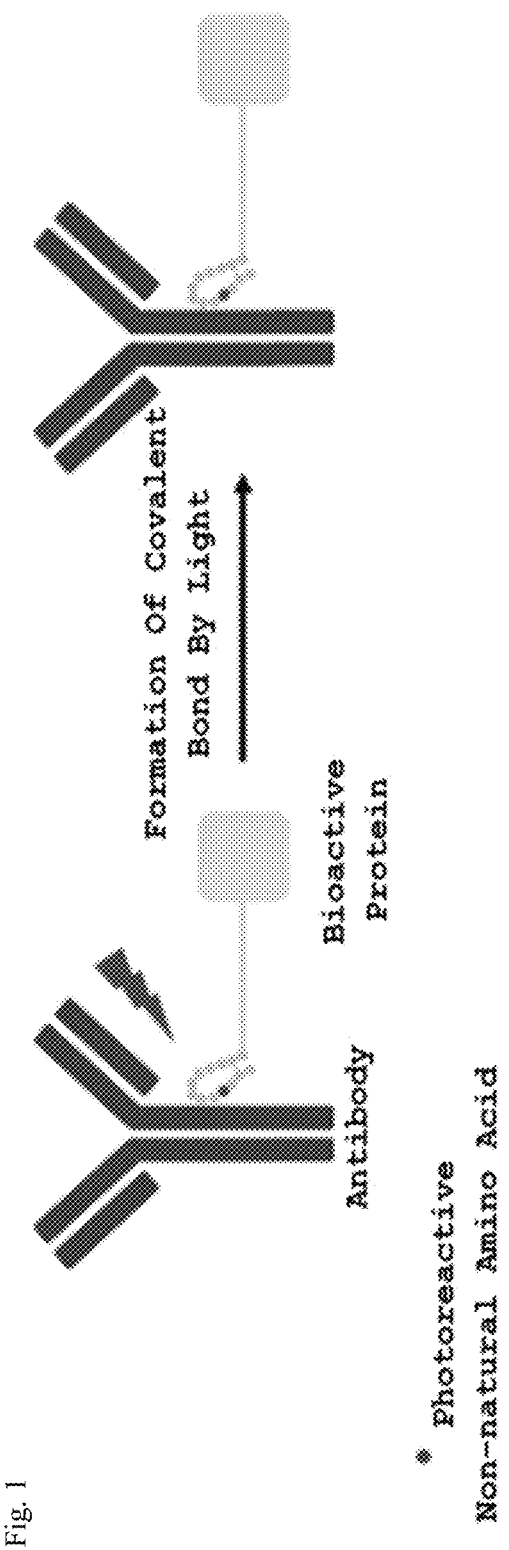
FIG. 1 is a scheme illustrating a technique for conjugation of an antibody and a substance according to the present invention.
Figure 2:
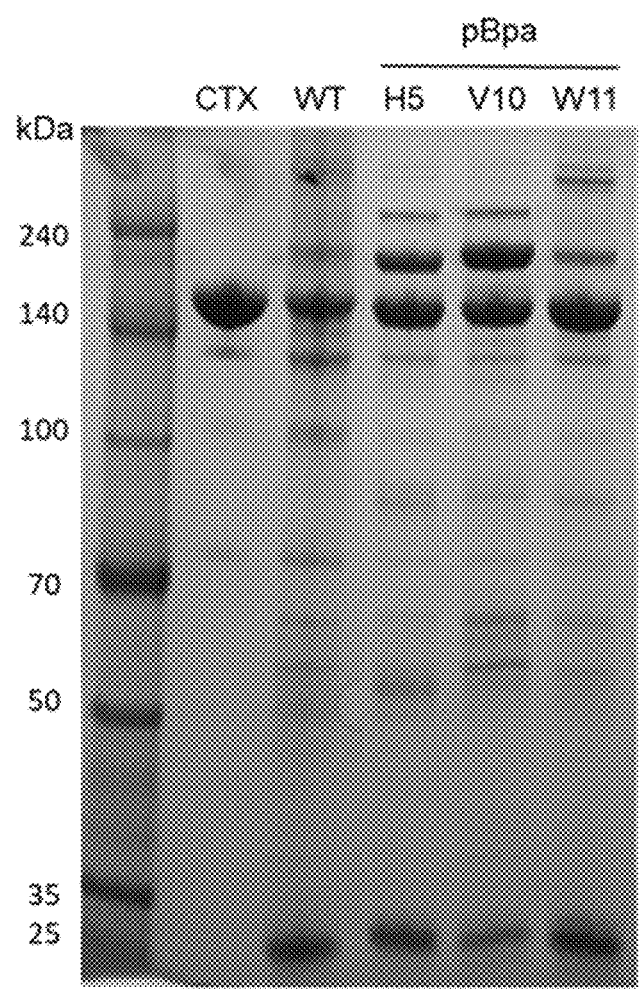
FIG. 2 illustrates electrophoresis results after a photoreaction between an antibody and a substance modified with a photoreactive peptide of the present invention in order to determine a substitution site of p-benzoyl phenylalanine in the Fc binding peptide (SEQ ID NO: 1).

In the present invention, as a result of covalently linking a substance modified with an Fc site-specific conjugating peptide in which position 5, 10, or 11 of an Fc binding peptide is substituted with an amino acid having a photoreactive functional group, to an antibody, it was confirmed that, unlike conventional antibody binding peptides, irreversible chemical bonds were formed, and the conjugation efficiency of the substance modified with the conjugating peptide to the antibody was enhanced depending on the introduction site of the photoreactive functional group (see FIG. 2).

Therefore, in one aspect, the present invention relates to an Fc site-specific conjugating peptide in which position 5, 10, or 11 in an Fc binding peptide represented by an amino acid sequence of SEQ ID NO: 1 is substituted with an amino acid having a photoreactive functional group.

In the present invention, the Fc binding peptide (amino acid sequence of SEQ ID NO: 1, gene sequence of SEQ ID NO: 2) is a short peptide consisting of 13 amino acids that site-specifically bind to the CH3-CH2 interface region of the Fc domain of a human-derived antibody (IgG1) (W. L. DeLano et al, *Science,* 2000). The peptide has a U-shaped structure because two cysteines form a disulfide bond.

In the present invention, the position of substitution with an amino acid having a photoreactive functional group may be position 10.

In the present invention, the Fc site-specific conjugating peptide substituted with an amino acid having a photoreactive functional group may be produced by identifying the amino acid sequence of an Fc binding peptide, expressing the peptide using a known method, for example, by constructing an expression vector capable of expressing the peptide, transforming the vector into a host cell, and expressing the peptide using a recombination technique, or may be produced by performing artificial synthesis, and then substituting at least one amino acid residue with an amino acid having a photoreactive functional group or introducing the same, or may be synthesized by including an amino acid having at least one photoreactive functional group in the artificial synthesis.

The introduction of the gene may be performed using a commonly known genetic manipulation method. For example, physical methods such as a method using a vector such as a virus, a non-viral method using a synthetic phospholipid or a synthetic cationic polymer, and an electric permeation method for introducing a gene by applying a temporary electrical stimulus to a cell membrane may be used, but the present invention is not limited thereto.

In the present invention, "amplification" conceptually encompasses mutation, substitution, or deletion of a certain base of the corresponding gene, introduction of a certain base, or introduction of a gene derived from another microorganism encoding the same enzyme to increase the activity of the corresponding enzyme.

In the present invention, "vector" means a DNA construct containing a DNA sequence operably linked to a suitable regulatory sequence capable of expressing DNA in a suitable host. The vector may be a plasmid, a phage particle, or simply a potential genomic insert. Once the vector is transformed into a suitable host, the vector can replicate and function independently of the genome of the host, or in some cases, may be integrated with the genome itself. Since plasmids are currently the most commonly used form of vector, the terms "plasmid" and "vector" may be used interchangeably throughout the specification of the present invention. However, the present invention includes other forms of vectors having functions identical to those already known or yet to be known in the art.

In the present invention, "expression vector" commonly refers to a recombinant carrier, into which a fragment of heterologous DNA is inserted, and generally means a fragment of double-stranded DNA. Here, the heterologous DNA refers to exogenous DNA that is not naturally found in the host cell. Once an expression vector is present in a host cell, the expression vector can replicate independently of the host chromosomal DNA, and several copies of the vector and inserted (heterologous) DNA thereof may be produced. As is well known in the art, in order to increase the expression level of a transgene in a host cell, the gene must be operably linked to a transcriptional/translational expression regulatory sequence that functions in a selected expression host. Preferably, the expression regulatory sequence and the corresponding gene are included in one expression vector including a bacterial selection marker and a replication origin. When the expression host is a eukaryotic cell, the expression vector should further include a useful expression marker in the eukaryotic expression host.

In the present invention, "integrated vector" refers to a vector whose integration or insertion into a nucleic acid is performed via an integrase. Examples of integrated vectors include, but are not limited to, retroviral vector, and transposon- and adeno-related viral vectors.

Another embodiment of the present invention provides a host cell transformed or transfected with the vector. The term "transformation" as used herein means introducing DNA into a host and making the DNA replicable by an extrachromosomal factor or chromosomal integration. This includes any method of introducing a nucleic acid into an organism, cell, tissue Or organ, and may be performed by selecting standard techniques suitable for the host cell, as is well known in the art. These methods include electroporation, protoplast fusion, calcium phosphate ($CaPO_4$) precipitation, calcium chloride ($CaCl_2$)) precipitation, agitation with silicon carbide fibers, agrobacteria-mediated transformation, PEG, dextran sulfate, lipofectamine, and drying/inhibition-mediated transformation methods, but the present invention is not limited thereto. The host cell of the present invention may be a prokaryotic or eukaryotic cell. In addition, a host having high DNA introduction efficiency and high expression efficiency of the introduced DNA is usually used. Examples of the host cell that can be used include well-known eukaryotic and prokaryotic hosts such as *E. coli, Pseudomonas, Bacillus, Streptomyces*, fungi, and yeast, insect cells such as those of *Spodoptera frugiperda* (SF9), animal cells such as CHO and mouse cells, African green monkey cells such as COS 1, COS 7, BSC 1, BSC 40, and BMT 10, and tissue-cultured human cells.

Of course, it should be understood that not all vectors function identically in expressing the DNA sequences of the present invention. Similarly, not all hosts function identically for the same expression system. However, those skilled in the art will be able to make appropriate selection from among a variety of vectors, expression regulatory sequences, and hosts without excessive burden of experimentation and without departing from the scope of the present invention. For example, selection of a vector should be carried out in consideration of the host because the vector must replicate therein. The number of replications of the vector, the ability to control the number of replications, and the expression of other proteins encoded by the corresponding vector, such as the expression of antibiotic markers, should also be considered. In selecting the expression regulatory sequence, various factors need to be considered. For example, the relative strength of the sequence, possibility of regulation, and compatibility with the DNA sequence of the present invention should be considered, particularly in relation to possible secondary structures. A single-cell host may be selected in consideration of factors such as the selected vector, the toxicity of the product encoded by the DNA sequence according to the present invention, the secretion characteristics, the ability to accurately fold proteins, culture and fermentation factors, and ease of purification of the product encoded by the DNA sequence according to the present invention. Within the scope of these variables, those skilled in the art can select various vector/expression regulatory sequence/host combinations capable of expressing the DNA sequences of the present invention in fermentation or large-scale animal culture. As a screening method for cloning cDNA of NSP proteins through expression cloning, a binding method, a panning method, a film emulsion method, or the like may be applied.

In the present invention, "protoplast fusion" refers to a technique for removing the cell wall of a protoplast, such as plant cells or bacteria, and fusing two cells with different traits using the protoplast. For protoplast fusion, there are chemical methods such as adding a metal ion such as calcium or magnesium to a high concentration of an osmotic solution, or physical methods such as exposing a protoplast to an electric shock to temporarily create small pores in the cell membrane, thereby increasing DNA absorption of the protoplast.

In the present invention, the "photoreactive functional group" may be a functional group capable of absorbing light of a specific wavelength upon light irradiation to form a covalent bond with an adjacent reactive functional group.

When the Fc site-specific conjugating peptide having a photoreactive functional group according to the present invention, is mixed with an antibody, the conjugating peptide is located adjacent to or binds to the Fc domain of the antibody, due to its binding specificity which is an inherent property thereof. Thereafter, when the mixture is irradiated with light, the mixture may absorb light of a specific wavelength and thereby form a covalent bond, through the photoreactive functional group, with a residue having a group reactive toward the photoreaction on the Fc domain of the antibody, adjacent thereto. That is, the Fc site-specific conjugating peptide of the present invention may be covalently linked to a specific functional group of the Fc domain through the photoreactive functional group upon light irradiation.

In the present invention, the amino acid having a photoreactive functional group may be p-benzoyl phenylalanine. An artificial amino acid having a photoreactive functional group may comprise photo-leucine, photo-methionine, azidophenylalanine, or the like, but the photoreactive functional group used in the present invention preferentially acts on a specific functional group and has specificity in that covalent bonds are activated through light of a long wavelength, i.e., low light energy.

p-Benzoyl phenylalanine of the present invention is represented by Formula 1 below.

[Formula 1]

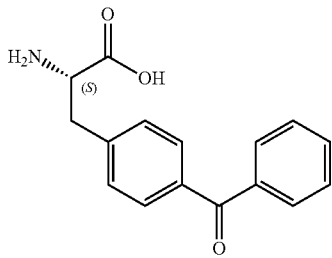

In another aspect, the present invention relates to a substance modified with a conjugating peptide wherein the substance is linked to the above-described peptide, either directly or via a linker.

In the present invention, the substance may be a therapeutic agent or a diagnostic agent, and the therapeutic or diagnostic agent may be selected from the group consisting of an enzyme, a hormone, a cytokine, an antibody, an antibody fragment, an analgesic, an antipyretic, an anti-inflammatory agent, an antibiotic, an anti-viral agent, an antifungal drug, a cardiovascular drug, a drug that acts on the central nervous system, a drug that affects renal function and electrolyte metabolism, and a chemotherapeutic agent.

The substance of the present invention may be a therapeutic agent or a diagnostic/detection agent. Particularly, the antibody used as the substance may be a therapeutic antibody. About 30 types of therapeutic antibodies are currently approved by the FDA, and the safety thereof is very high due to properties that are almost the same as those of IgG present in vivo. Antibodies are used as therapeutic agents for a wide range of disorders (e.g., transplant rejection, cancer, autoimmune diseases and inflammation, heart diseases, and infections). In particular, when an Fc domain-containing molecule is a therapeutic antibody, the therapeutic antibody recognizes and binds to a receptor protein or antigen protein specifically present in diseased tissues, and thus has very high specificity. Thus, when a molecular imaging probe or a drug carrier is combined as a substance with a therapeutic antibody, this may be converted into a theragnosis agent capable of monitoring a treatment process and a drug combination effect. In addition, by combining a molecular imaging probe or a drug delivery system with a simple targeting antibody, it is possible to develop a theragnosis agent for diagnosis, treatment, or simultaneous diagnosis and treatment.

Non-limiting examples of therapeutic agents include antibodies, antibody fragments, drugs, toxins, nucleases, hormones, immunomodulators, chelators, boron compounds, photoactive agents or dyes, and radioactive isotopes.

Non-limiting examples of diagnostic/detection agents include radioisotopes, dyes (e.g., biotin-streptavidin complex), contrast agents, fluorescent compounds or molecules, and enhancing agents (e.g., paramagnetic ions) for magnetic resonance imaging (MRI). Preferably, the diagnostic agent includes radioisotopes, enhancing agents for use in magnetic resonance imaging, and fluorescent compounds. To load an antibody component with radioactive metals or paramagnetic ions, it may be necessary to react the antibody component with a reagent having a long tail attached to a plurality of chelating groups for binding the ions. The tail may be a polymer such as polylysine or a polysaccharide, or a derivatized or derivatizable chain having pendant groups that can bind to chelating groups such as ethylenediaminetetraacetic acid (EDTA), diethylenetriaminepentaacetic acid (DTPA), porphyrin, polyamine, crown ether, bis-thiosemicarbazone, and polyoximes, and that is known to be useful for the above purpose. A chelate may be normally linked to the Fc site-specific conjugating peptide by a functional group which enables the formation of a bond to the molecule with minimal loss of immunoreactivity and minimal aggregation, and/or via internal crosslinking.

In particular, useful metal-chelate combinations include diagnostic isotopes, 2-benzyl-DTPA, and monomethyl and cyclohexyl analogs thereof used in a general energy range of 60 keV to 4,000 keV, and examples of radioactive imaging agents include $^{125}$I, $^{131}$I, $^{123}$I, $^{124}$I, $^{62}$Cu, $^{64}$Cu, $^{18}$F, $^{111}$In, $^{67}$Ga, $^{99}$mTc, $^{94}$mTc, $^{11}$C, $^{13}$N, $^{15}$O, and $^{76}$Br. In the case of being complexed with non-radioactive metals such as manganese, iron, and gadolinium, the same chelates are useful for MRI when used with nanoparticles or antibodies of the present invention. Macrocyclic chelates, such as NOTA, DOTA, and TETA, are used with types of metal and radiometals, preferably radionuclides of gallium, yttrium, and copper, respectively. The metal-chelate complex may be prepared very stably by fitting the size of ring to the corresponding metal. According to the present invention, cyclic chelates, such as macrocyclic polyethers useful for stably binding nuclides such as $^{223}$Ra to RAIT, may be prepared.

An immunoconjugate is a conjugate of an antibody component with a therapeutic or diagnostic agent. The diagnostic agent includes a radioactive or non-radioactive label and a contrast agent (a contrast agent suitable for magnetic resonance imaging, computed tomography, or ultrasound), and the radioactive label may be a gamma-, beta-, alpha-, Auger electron-, or positron-emitting isotope.

In the present invention, the "immunomodulator" typically stimulates immune cells to proliferate or become activated in an immune response cascade, such as macrophages, B-cells, and/or T-cells. An example of an immunomodulator is a cytokine. As will be obvious to those of ordinary skill in the art, interleukin and interferon are cytokines that stimulate the activity of T-cells or other immune cells.

Deoxyribonucleic acid (DNA), ribonucleic acid (RNA), peptide nucleic acid (PNA), or locked nucleic acid (LNA) may be linked directly or via a linker to the Fc site-specific conjugating peptide of the present invention. Since the DNA, RNA, PNA, and LNA are polymers having properties of specifically binding to a material having a complementary sequence, the Fc site-specific conjugating peptide to which the DNA, RNA, PNA or LNA is linked may be used in gene screening, biosensors, and the like.

The Fc site-specific conjugating peptide to which the DNA, RNA, PNA or LNA is linked may be immobilized on a solid support to be used as a biochip, biosensor, immunodetection kit, or complementary self-addressable chip.

In the present invention, the linker may comprise a reactive functional group, an amino acid, and a self-cleaving spacer.

The linker of the present invention may be in a form that links a specific residue in the Fc site-specific conjugating peptide substituted with a photoreactive functional group, with a substance, and may have a reactive site with an electrophilic group that reacts with the nucleophilic residue (e.g., cysteine) present on the Fc site-specific conjugating peptide substituted with a photoreactive functional group. The linker may comprise for example, a reactive functional group, an amino acid, and a self-cleaving spacer that binds to the Fc site-specific conjugating peptide substituted with a photoreactive functional group.

The functional group may be i) a maleimide group, an acetamide group, or derivatives thereof, ii) an aziridine group, an aryl halide, an acryloyl group, or derivatives thereof, or iii) an alkylating reactive group, an arylating reactive group, pyridyl disulfide, thionitrobenzoic acid, or derivatives thereof. Specifically, the linker may be in the form of: i) a maleimide group or derivative thereof-valine-citrulline-para-aniline benzoic acid (PABA); or ii) an acetamide group or derivative thereof-valine-citrulline-para-aniline benzoic acid (PABA), but the present invention is not limited thereto.

Binding of the Fc site-specific conjugating peptide substituted with a photoreactive functional group to the substance via the linker may be performed using a known method, for example, alkylation, disulfide exchange, or transthioesterification reaction. This enables conjugation of the conjugating peptide and the substance via a thiol group in the cysteine residue in the Fc site-specific conjugating peptide substituted with a photoreactive functional group.

In one embodiment, in the case of maleimide groups used for thiol-linker linkages, the nucleophilic reactivity of the thiol of the cysteine residue to the meleimide group is about 1,000 times greater than that of other amino acid functional groups present in proteins, e.g., amino groups or N-terminal amino groups of the lysine residue, and thus such maleimide groups may be used to specifically bind to cysteine. Thus, it can be seen that a substance modified with the conjugating peptide through a maleimide group or a derivative thereof or an acetamide group or a derivative thereof, for example, a bromo acetamide group or an iodo acetamide group, is linked to the Fc site-specific conjugating peptide substituted with a photoreactive functional group via a thioether bond of cysteine.

In another aspect, the present invention relates to a method of producing an antibody conjugate, comprising: (a) mixing a substance modified with the conjugating peptide with an Fc domain-containing molecule; (b) irradiating the mixture with light to induce a photoreaction and then to produce an antibody conjugate in which a photoreactive functional group of the substance modified with the conjugating peptide and the Fc domain-containing molecule are covalently linked; and (c) obtaining the produced antibody conjugate.

In the present invention, the light may be in a range from 320 nm to 380 nm, preferably 350 nm to 365 nm, but the present invention is not limited thereto.

In the present invention, "Fc domain-containing molecule" includes, without limitation, molecules containing an Fc domain that are specifically recognized by the Fc site-specific conjugating peptide and can be located adjacent thereto or can bind thereto. The Fc domain-containing molecule includes proteins, peptides, glycoproteins, glycopeptides, antibodies or fragments thereof, immunoglobulins or fragments thereof, and the like, which contain Fc domains. The antibodies and immunoglobulins are heterotetrameric glycoproteins of about 150 kDa, which include two identical light chains and two identical heavy chains. The fragments thereof containing an Fc domain may be fragments of antibodies or immunoglobulins treated with papain, from which light chains and heavy chains have been removed.

In the present invention, the Fc domain-containing molecule may be a targeted natural or non-natural antibody capable of specifically binding to a target molecule.

In the present invention, the antibody includes both polyclonal and monoclonal antibodies, as well as certain recombinant antibodies, such as chimeric, humanized or human antibodies. The antibodies may be receptor-specific antibodies or ligand-specific antibodies. In the present invention, the antibodies may also be receptor-specific antibodies that do not prevent ligand binding but prevent receptor activation. In addition, the antibodies may be therapeutic antibodies, antibodies that can bind to a separate therapeutic agent or diagnostic agent, antibodies for targeting that do not have therapeutic effects, or simply antibodies capable of performing an antigen-antibody reaction.

In the present invention, the antibody conjugate is a technology focused on a drug that particularly targets only specific tissue (e.g., cancer cells) by making the best use of advantages of antibodies, such as specificity, non-toxicity in circulation, and pharmacokinetics. Therefore, the antibody conjugate is also referred to as an immunoconjugate, and anticancer drugs for "targeted chemotherapeutics" fall within this range. The immunoconjugate consists of three components, including a drug, a monoclonal antibody, and a linker, which links the antibody and the drug. Particularly, for anticancer purposes, immunoconjugate technology is a method for delivering a substance having physiological activity to tumor cells using an antibody that specifically binds to a specific antigen expressed on the surfaces of cancer cells.

In one embodiment of the present invention, beta-lactamase (ß-lactamase (TEM-1)), beta-lactamase zymogen (Korean Patent Registration No. 1016956840000 (2017 Jan. 6)) and *Pseudomonas* exotoxin A (PE24) were used as substance compounds.

In the present invention, "ß-lactamase" (amino acid sequence of SEQ ID NO: 3) itself does not have cytotoxicity, but performs a mechanism for cleaving a prodrug having a beta-lactam ring to activate it as a drug, and thus, when co-treated with an appropriate prodrug, ß-lactamase may be used as an effective drug for treating tumors. In the present invention, an inactive prodrug called GC-mel may be used, and the β-lactam ring of GC-Mel is cleaved by β-lactamase, which is converted into a Melphalan form and alkylated to intracellular DNA, thereby inhibiting cell proliferation and causing cell apoptosis.

In the present invention, "ß-lactamase zymogen" (amino acid sequence of SEQ ID NO: 5) is expressed in an inactive state, in which beta-lactamase inhibitor protein (BLIP) is fused with ß-lactamase and expressed together. For example, however, a matrix metalloproteinase-2 (MMP-2) cleavage site, which is overexpressed in cancer cells, is introduced in a linker via which two proteins are linked, and thus BLIP is cleaved and removed in the vicinity of cancer cells, and consequently ß-lactamase exhibits activity; MMP-2 is overexpressed in cancer cells.

In the present invention, "PE24" (amino acid sequence of SEQ ID NO: 7) inactivates elongation factor-2 (EF-2) through ADP-ribosylation, which is involved in intracellular protein synthesis, thereby causing cell apoptosis (U.S. Pat. No. 9,388,222 (2016 Jul. 12)).

In the present invention, the Fc domain-containing molecule may be selected from the group consisting of immunoglobulin-derived domains, combinations thereof, and Fc regions thereof. Preferably, the Fc domain-containing molecule may be selected from the group consisting of IgG, IgA, IgD, IgE, IgM, combinations thereof, and Fc regions thereof, and more preferably, may be IgG1 or an Fc region thereof, but the present invention is not limited thereto.

According to the present invention, in the obtaining of the produced antibody conjugate (process (c) above), since the Fc conjugating peptide binds to the Fc domain of a heavy chain of the antibody, when a photoreaction occurs between a fusion protein and the antibody, a total of three products (an unbound antibody, a form in which a substance modified with the Fc conjugating peptide is linked to the antibody, and a form in which two substances modified with the Fc conjugating peptide are linked to the antibody) may be obtained. In order to be used as a therapeutic drug, it is necessary to obtain a product having well-defined structures, and thus, one form must be isolated among the three reaction products. The antibody conjugate in which a substance modified with the Fc conjugating peptide is linked to the antibody has one binding site for the neonatal Fc receptor (FcRn) and can have a loner half-life time in circulation than the form in which two substances are linked the antibody masking the all two FcRn binding site.

The presence of unconjugated antibody may be prohibited under a reaction condition optimized for the substance and antibody concentrations, the ratio of the two reactants, the reaction temperature, the UV irradiation time, etc.

The antibody conjugates in which a substance modified with the Fc conjugating peptide is linked to an antibody and the antibody conjugate in which two substances modified with the Fc conjugating peptide are linked to the antibody may be separated from each other using the binding affinity between protein A and the Fc domain of the antibody. Protein A has a specific binding affinity to the $CH_2$—$CH_3$ domain interface of the Fc domain of the antibody, and thus is used as a resin for affinity chromatography, which is used for purification after the antibody is expressed. Thus, the antibody conjugate, in which two substances modified with the Fc conjugating peptide are linked to the antibody, does not bind to the protein A resin (W. L. DeLano et al, *Science*, 287(5456):1279-83, 2000). The form in which two substances are linked to the antibody may be removed through protein A affinity chromatography, and then anion chromatography may be further performed on the resultant product, thereby separating the unconjugated antibody and the form in which a substance modified with the Fc conjugating peptide is linked to the antibody due to the difference in the isoelectric point thereof.

In another aspect, the present invention relates to an antibody conjugate in which an antibody is covalently linked to a substance modified with the Fc conjugating peptide.

In another embodiment of the present invention, to confirm the activity of an IgG1-FcIII-PE24 conjugate, WST-8 assay and MTS assay were performed. In the WST-8 and MTS assays, a tetrazolium salt in a solution is changed into formazan by mitochondrial succinate dehydrogenase in media, which enables measurement at a specific absorbance, and thus cell viability can be confirmed through the absorbance measurement. A change in absorbance was measured by increasing the concentrations of the antibody conjugate within a specific range. As a result, it was observed that, as the concentration of the antibody conjugate in which the antibody and a substance modified with the Fc conjugating peptide were linked was increased, cell viability decreased. Thus, it was confirmed that the antibody conjugate of the present invention can be used as a therapeutic drug.

In the present invention, as an example of commercial human IgG, antibody conjugates were prepared using cetuximab or trastuzumab, and purified to confirm the activity thereof. Trastuzumab inhibits the activation of EGFR (EGF, TGFα) or HER4 (NRG1), which are dependent on ligands, by specifically acting on HER2, which forms a heterodimer with EGFR or HER4 and prevents downstream signaling. In addition, cetuximab inhibits the activation of EGFR, which is dependent on ligands (EGF, TGFα), and prevents downstream signaling.

Hereinafter, the present invention will be described in further detail with reference to the following examples. These examples are provided for illustrative purposes only, and it will be obvious to those of ordinary skill in the art that these examples should not be construed as limiting the scope of the present invention.

Example 1: Production of Fc Site-Specific Conjugating Peptide

To select a substitution position of p-benzoyl phenylalanine capable of performing efficient photoreaction binding, an Fc binding peptide variant in which the DNA nucleotide sequence at position 5, 10, or 11 in the amino acid sequence of SEQ ID NO: 1 was substituted with an amber codon was subjected to gene synthesis (Bioneer), followed by genetic manipulation so that the peptide can be expressed in the form of a fusion protein. The resulting peptide was expressed such that p-benzoyl phenylalanine is inserted at the amber codon position of the Fc binding peptide variants, and then purified. To observe a change in photoreaction efficiency according to the substitution position, human IgG1 and each of substances modified with the Fc binding peptide variant in which a DNA nucleotide sequence at position 5 of the above amino acid sequence is substituted with an amber codon (amino acid sequence of SEQ ID NO: 11, gene sequence of SEQ ID NO: 12), the Fc binding peptide variant in which a DNA nucleotide sequence at position 10 is substituted with an amber codon (amino acid sequence of SEQ ID NO: 13, gene sequence of SEQ ID NO: 14), and the Fc binding peptide variant in which a DNA nucleotide sequence at position 11 is substituted with an amber codon (amino acid sequence of SEQ ID NO: 15, gene sequence of SEQ ID NO: 16) were mixed in a ratio of 1:3 to thereby prepare samples, and then the samples were irradiated with ultraviolet light of 365 nm for 2 hours using a UV hand lamp (Lklab, U01-133-194) in a 1×PBS buffer (pH 7.4).

As a result, it was confirmed that the substance modified with the Fc binding peptide variant in which valine, which is the $10^{th}$ amino acid, is substituted with p-benzoyl phenylalanine exhibited the highest binding efficiency to the antibody (see FIG. 2). Accordingly, the sample, in which the position of valine (the 10th amino acid) is substituted with p-benzoyl phenylalanine, exhibits the highest photoreaction efficiency, and the variant was names as 'Fc site-specific conjugating peptide.'

To construct a plasmid to express the Fc site-specific conjugating peptide, a peptide gene in which the 10th amino acid is substituted with an amber codon was cleaved with NheI in a 2.1 NEB buffer and then with BamHI in a 3.1 NEB buffer. The buffer consisted of DDW, 10×NEB buffer 3.1, DNA, and a restriction enzyme and had a total volume of 50 al, and treatment conditions were as follows: 37° C. for 4 hours. A pET21-a vector cleaved with the same restriction enzymes as described above to have both sticky ends and the cleaved peptide and plasmid genes were mixed in a molar ratio of 1:3 to a total volume of 10 µl, followed by ligation using T4 DNA ligase (NEB, England) at room temperature for 2 hours.

The ligated DNA mixed solution was mixed with 50 µl of E. coli DH10B (Thermo Scientific, C640003), which is a competent cell, to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the Fc site-specific conjugating peptide expression plasmid-1.

In addition, the same peptide gene in which the 10th amino acid is substituted with an amber codon was cloned into pET22-b using NdeI and NcoI following the same procedure above, and the resulting plasmid was named as plasmid-2.

Example 2: Preparation of Substance Modified with Conjugating Peptide

Example 2-1: FcIII-ß-Lactamase Cloning

As a template, a plasmid (pSPEL104) containing the entire sequence of ß-lactamase represented by SEQ ID NO: 4 was amplified through polymerase chain reaction (PCR) using primers shown in Table 1, and then cleaved with restriction enzymes BamHI and NotI and ligated to the Fc site-specific conjugating peptide expression plasmid-1.

PCR undergoes three stages of denaturation, annealing, and amplification, and the method is as follows. The reaction composition of PCR includes DDW, 10× pfu buffer, 0.2 mM dNTP, 20 pmol primers F/R, template, and 5 units Pfu polymerase, and the final reaction volume is 50 µl. After reacting at 95° C. for 2 minutes using BamhI-TEM1-f and TEM1-NotI-r of Table 1, the reaction product was subjected to 25 cycles of PCR, wherein the condition of one cycle was as follows: 95° C. for 30 seconds, 55° C. for 30 seconds, and 72° C. for 1 minute. After reaction completion, treated was performed at 72° C. for 10 minutes.

Table 1 shows PCR primers used in the present invention.

TABLE 1

| BamhI-TEM1-f | aaccttGGATCCggcggtggcagcgaaacgct ggtgaaagtaaaagatg (SEQ ID NO: 24) |
|---|---|
| TEM1-NotI-r | AAGGTTgcggccgctTTAttaccaatgcttaa tcagtga (SEQ ID NO: 25) |

TABLE 1-continued

| NdeI-FcIII V10*-f | AACCTTcatatgAAGAAAACAGCAATTGCTAT TG (SEQ ID NO: 26) |
|---|---|
| FcIII V10*-NcoI-r | AAGGTTccatggTGTACACCActaTAATTCAC C (SEQ ID NO: 27) |
| NcoI-ß-lactamase zymogen-f | aaccttCCATGGggcggtATGGACGAGCGTAA CCGTCAAA (SEQ ID NO: 28) |
| ß-lactamase zymogen-NotI-r | aaggttGCGGCCGCTttaTACAAGGTCCCACT GCCGCTTG (SEQ ID NO: 29) |

Cleavage was performed by treatment with the two restriction enzymes in a 3.1 NEB buffer. The buffer consisted of DDW, 10×NEB buffer 3.1, DNA, and a restriction enzyme and had a total volume of 50 µl, and treatment conditions were as follows: 37° C. for 4 hours. The Fc site-specific conjugating peptide expression plasmid-1 cleaved with the same restriction enzyme as described above to have both sticky ends and γ-lactamase were mixed in a molar ratio of 1:3 to a total volume of 10 µl, followed by ligation using T4 DNA ligase (NEB) at 25° C. for 2 hours.

Figure 3:
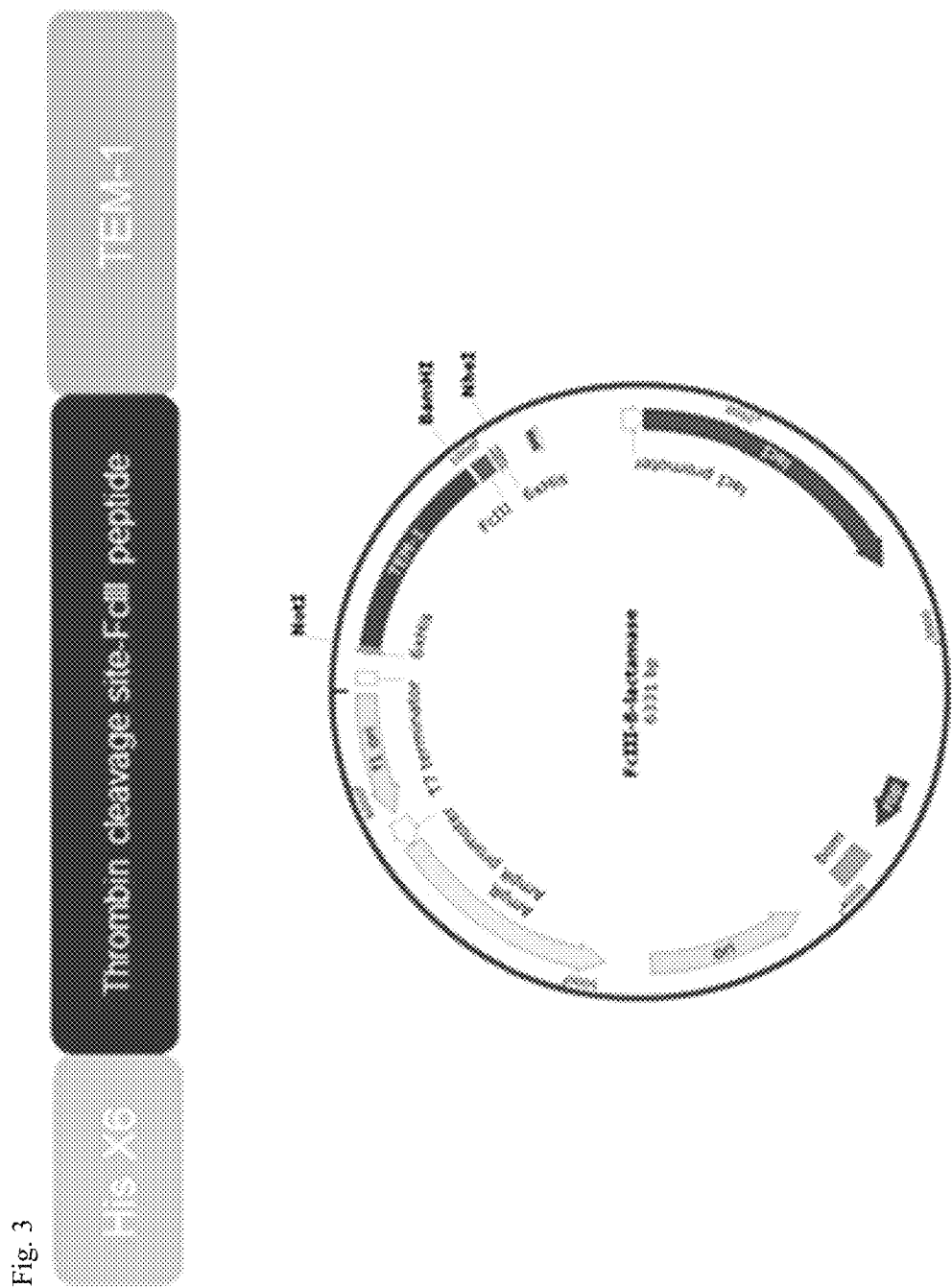
FIG. 3 is a schematic view illustrating a plasmid expressing ß-lactamase modified with the Fc conjugating peptide of the present invention (FcIII-ß-lactamase) and FcIII-ß-lactamase expressed in the plasmid.

The ligated DNA mixed solution was mixed with 50 µl of E. coli DH10B (Thermo Scientific, C640003), which is a competent cell, to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-ß-lactamase (amino acid sequence of SEQ ID NO: 17, gene sequence of SEQ ID NO: 18)-expressing plasmid (see FIG. 3).

Example 2-2: FcIII-ß-Lactamase Zymogen Cloning

As a template, a plasmid (pSPEL166) containing the ß-lactamase zymogen sequence (1353 bp) represented by SEQ ID NO: 6 was amplified through PCR using the primers of Table 1 under the same conditions as described above, and then cleaved with restriction enzymes NcoI and NotI, followed by ligation to the Fc site-specific conjugating peptide expression plasmid-2 in the same manner as described above.

Figure 4:
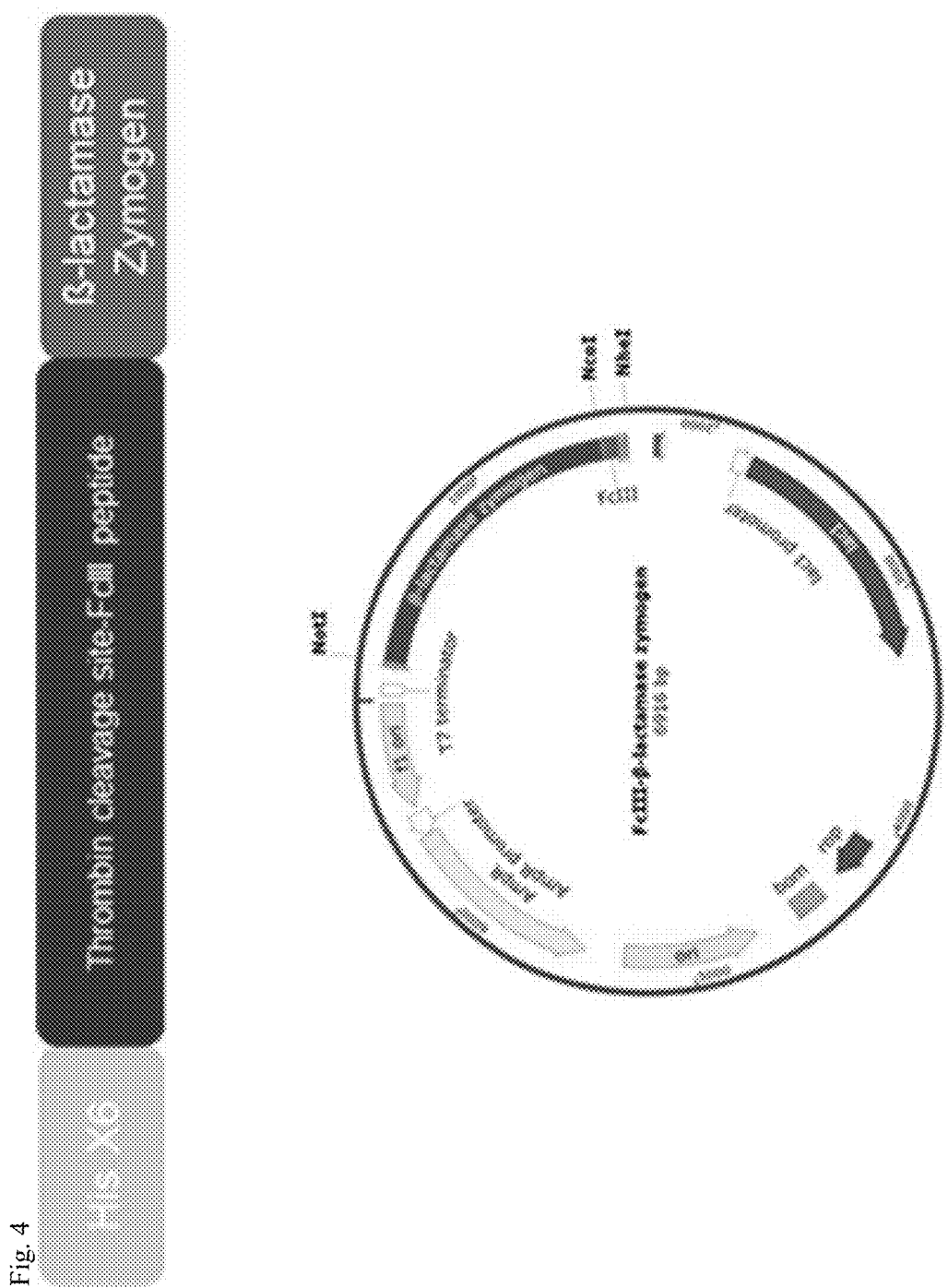
FIG. 4 is a schematic view illustrating a plasmid expressing ß-lactamase zymogen modified with the Fc conjugating peptide of the present invention (FcIII-ß-lactamase zymogen) and FcIII-ß-lactamase zymogen expressed in the plasmid.

The ligated DNA mixed solution was added to and mixed with 50 µl of E. coli DH10B (Thermo Scientific, C640003) to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-ß-lactamase zymogen (amino acid sequence of SEQ ID NO: 19, gene sequence of SEQ ID NO: 20)-expressing plasmid (see FIG. 4).

Example 2-3: FcIII-PE24 Cloning

Deimmunized PE24 represented by SEQ ID NO: 8 was obtained by gene synthesis (Bioneer), and then cleaved with restriction enzymes BamHI and NotI using the same method as that used above, followed by ligation to the Fc site-specific conjugating peptide expression plasmid-1.

Figure 5:
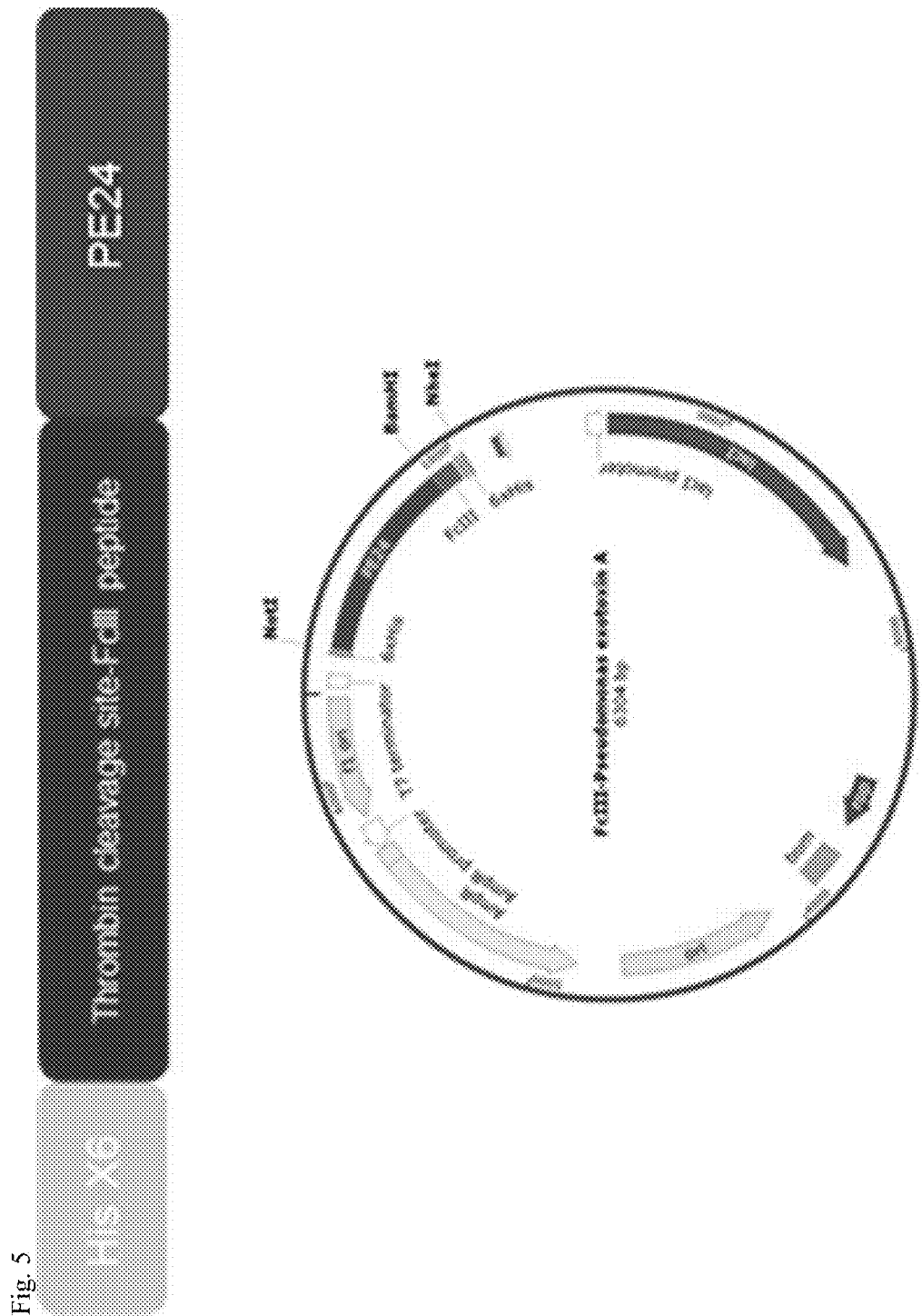
FIG. 5 is a schematic view illustrating a plasmid expressing PE24 modified with the Fc conjugating peptide of the present invention (FcIII-PE24) and FcIII-PE24 expressed in the plasmid.

The ligated DNA mixed solution was added to and mixed with 50 µl of E. coli DH10B (Thermo Scientific, C640003) to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-PE24 fusion protein (amino acid sequence of SEQ ID NO: 21, gene sequence of SEQ ID NO: 22)-expressing plasmid (see FIG. 5).

Example 2-4: Orthogonal TAG Codon Recognition tRNA and tRNA Synthetase Cloning

Figure 6A:
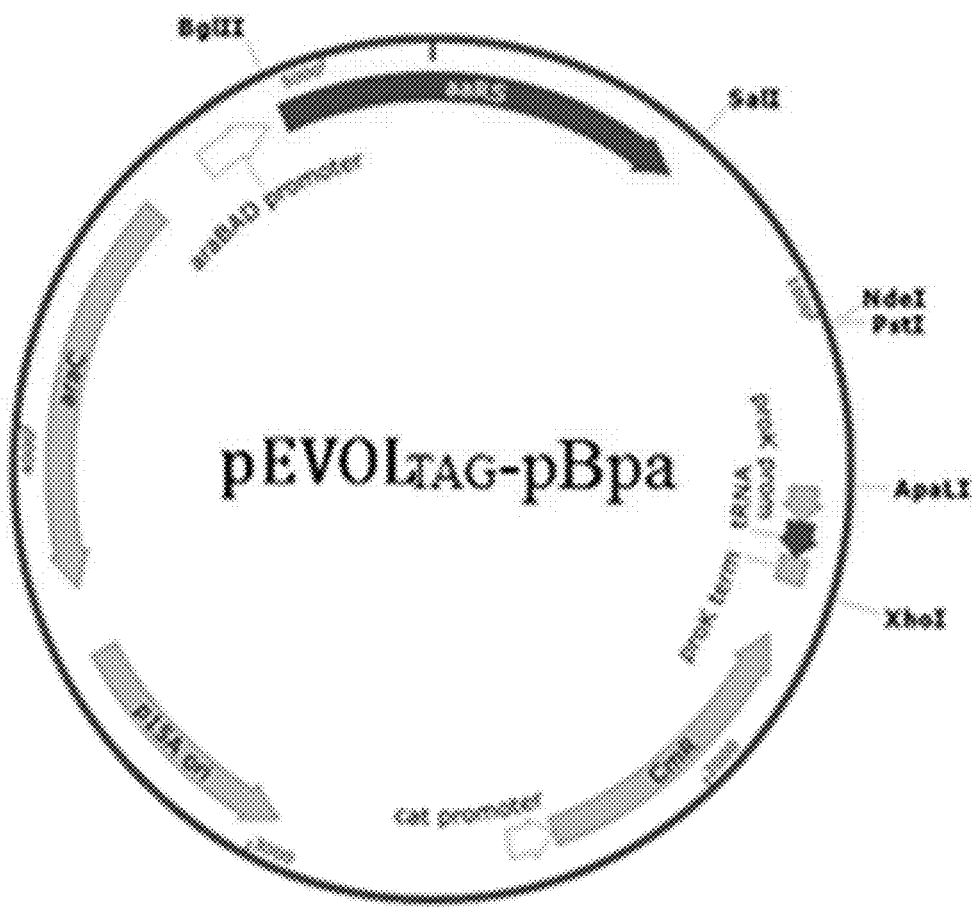
FIG. 6a illustrates a recombinant tRNA synthetase-expressing plasmid according to the present invention.

A p-benzoyl phenylalanine tRNA synthetase (amino acid sequence of SEQ ID NO: 9) sequence represented by SEQ ID NO: 10 was cleaved with SalI and BglII, and then ligated using, as a vector, a pEVOL plasmid including a tRNA sequence recognizing the TAG codon (Jason W. Chin et al, *PNAS vol.* 99, 11020-11024, 2002) (see FIG. 6a).

The ligated DNA mixed solution was added to and mixed with 50 μl of *E. coli* DH10B (Thermo Scientific, C640003) to perform electroporation (Bio-Rad, USA). Subsequently, the mixture was spread on chloramphenicol-containing LB agar medium and cultured at 37° C. for 12 to 14 hours to obtain a transformed strain, followed by DNA prep (Gene-All, mini prep kit) to thereby obtain the plasmid expressing tRNA synthetase (gene sequence of SEQ ID NO: 23) that inserts p-benzoyl phenylalanine by recognizing the TAG codon.

Figure 6B:
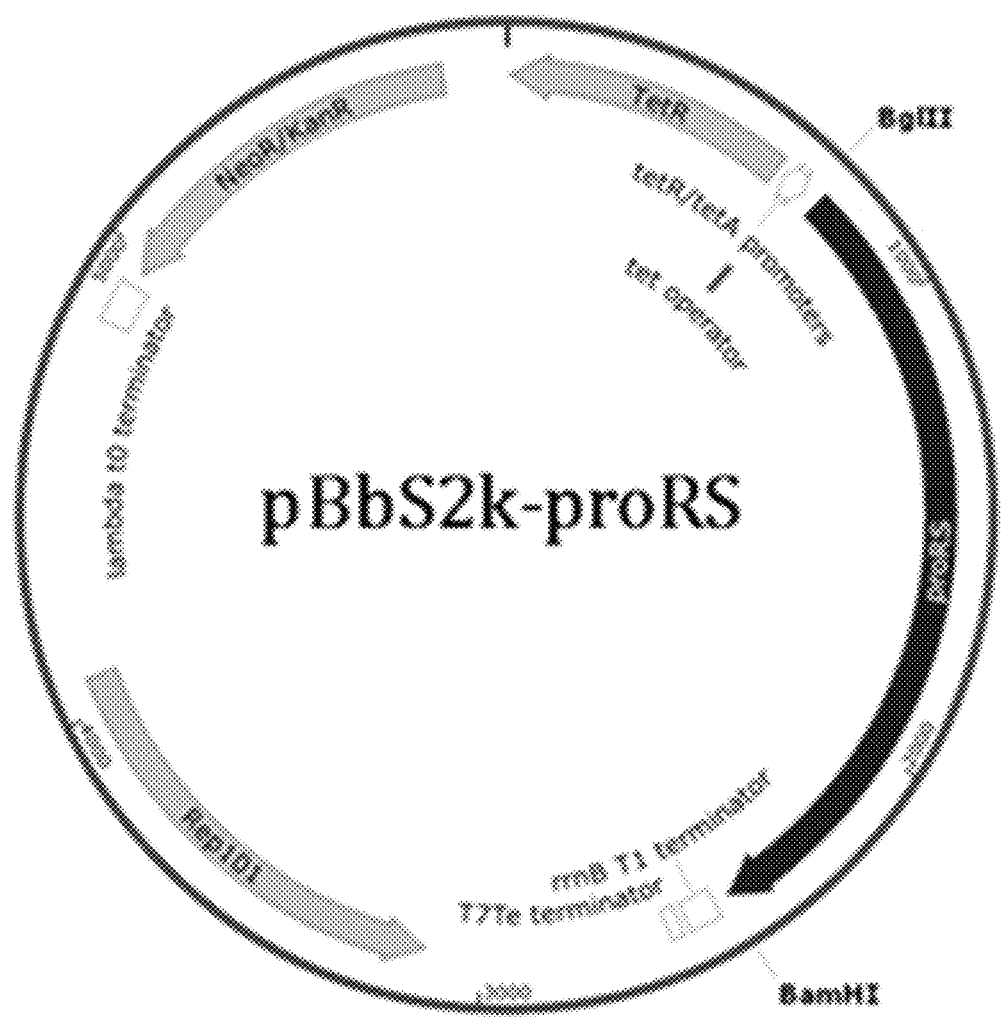
FIG. 6b illustrates a proline tRNA synthetase-expressing plasmid.

In the present invention, a pBbS2K plasmid containing a proline tRNA synthetase sequence was used (Byeong Sung Lee et al, *Biochimica Biophysica Acta*, S0304-4165, 2017) (see FIG. 6b).

Example 3: Expression and Purification of Substance Modified with Conjugating Peptide Example 3-1: Expression and Purification of FcIII-ß-Lactamase For the expression of FcIII-ß-lactamase, the FcIII-ß-lactamase-expressing plasmid, the plasmid containing a pair of TAG codon recognition tRNA and p-benzoyl phenylalanine tRNA synthetase, and the plasmid containing proline tRNA synthetase were subjected to electroporation into *E. coli* BL21 (DE3) (SIGMA Aldrich, CMC0016), and then the resulting mixture was spread on an LB plate containing ampicillin, chloramphenicol, and kanamycin to thereby obtain a transformed strain.

The obtained single colony as a seed was seed-cultured at 37° C. and 180 rpm for 12 hours, and inoculated again in a medium in a ratio of 10:1, followed by incubation at 37° C. and 180 rpm for 6 hours. 200 ml of a 2×YT (containing ampicillin, chloramphenicol, and kanamycin) was inoculated with the culture solution in a ratio of 100:1, and then incubated at 37° C. and 180 rpm, and when the absorbance at 600 nm reached 0.5, arabinose was added to a final concentration of 0.2%, and anhydrotetracycline (aTc) was added thereto to 20 nM. When the absorbance reached 1.0, p-benzoyl phenylalanine 1 mM and isopropyl-β-D-thiogalactoside (IPTG) 1 mM were added as a final concentration, followed by incubation at 37° C. and 180 rpm over 12 hours.

To purify the expressed FcIII-ß-lactamase, centrifugation was performed at 4° C. and 9300 g for 15 minutes. Subsequently, the supernatant was removed, followed by resuspension in 5 ml of a lysis buffer (0.75 M sucrose, 0.1 Tris, pH 8.0), addition of 0.05 g/ml of lysozyme and 10 ml of 1 mM EDTA, and rotating at 4° C. for 20 minutes. Thereafter, 1 ml of 0.5 M MgCl$_2$ was added thereto, followed by rotating at 4° C. for 10 minutes and centrifugation at 4° C. and 9300 g for 15 minutes, and the supernatant was separated.

Thereafter, to purify a histidine-tagged protein, 1 ml of a 50% Ni-NTA Superflow resin (Clonetech, USA) slurry was added to 20 ml of the supernatant, and while rotating at 4° C. for 1 hour, FcIII-ß-lactamase was allowed to bind to the resin. After loading the reaction solution on an empty column, washing was performed by loading 30 ml of a washing buffer (50 mM NaPO$_3$, 300 mM NaCl, 40 mM imidazole), and 5 ml of an elution buffer (50 mM NaPO$_3$, 300 mM NaCl, 300 mM imidazole) was loaded to elute 6× His-tag FcIII-ß-lactamase.

Example 3-2: Expression and Purification of FcIII-ß-Lactamase Zymogen

For the expression of FcIII-ß-lactamase zymogen, the FcIII-ß-lactamase zymogen-expressing plasmid, the plasmid containing a pair of TAG codon recognition tRNA and p-benzoyl phenylalanine tRNA synthetase, and the plasmid containing proline tRNA synthetase were subjected to electroporation into *E. coli* BL21 (DE3) (SIGMA Aldrich, CMC0016), followed by culture in the same manner as in the expression of FcIII-ß-lactamase, thereby expressing FcIII-ß-lactamase zymogen.

Subsequently, purification was performed under the same conditions as those of the purification of FcIII-ß-lactamase, to elute 6× His-tag FcIII-ß-lactamase zymogen.

Example 3-3: Expression and Purification of FcIII-PE24

For the expression of FcIII-PE24, the FcIII-PE24-expressing plasmid, the plasmid containing a pair of TAG codon recognition tRNA and p-benzoyl phenylalanine tRNA synthetase, and the plasmid containing proline tRNA synthetase were subjected to electroporation into *E. coli* BL21 (DE3) (SIGMA Aldrich, CMC0016), followed by culture in the same manner as in the expression of FcIII-ß-lactamase, thereby expressing FcIII-PE24.

Subsequently, purification was performed under the same conditions as those of the purification of FcIII-ß-lactamase, to elute 6× His-tag FcIII-PE24.

Figure 7:
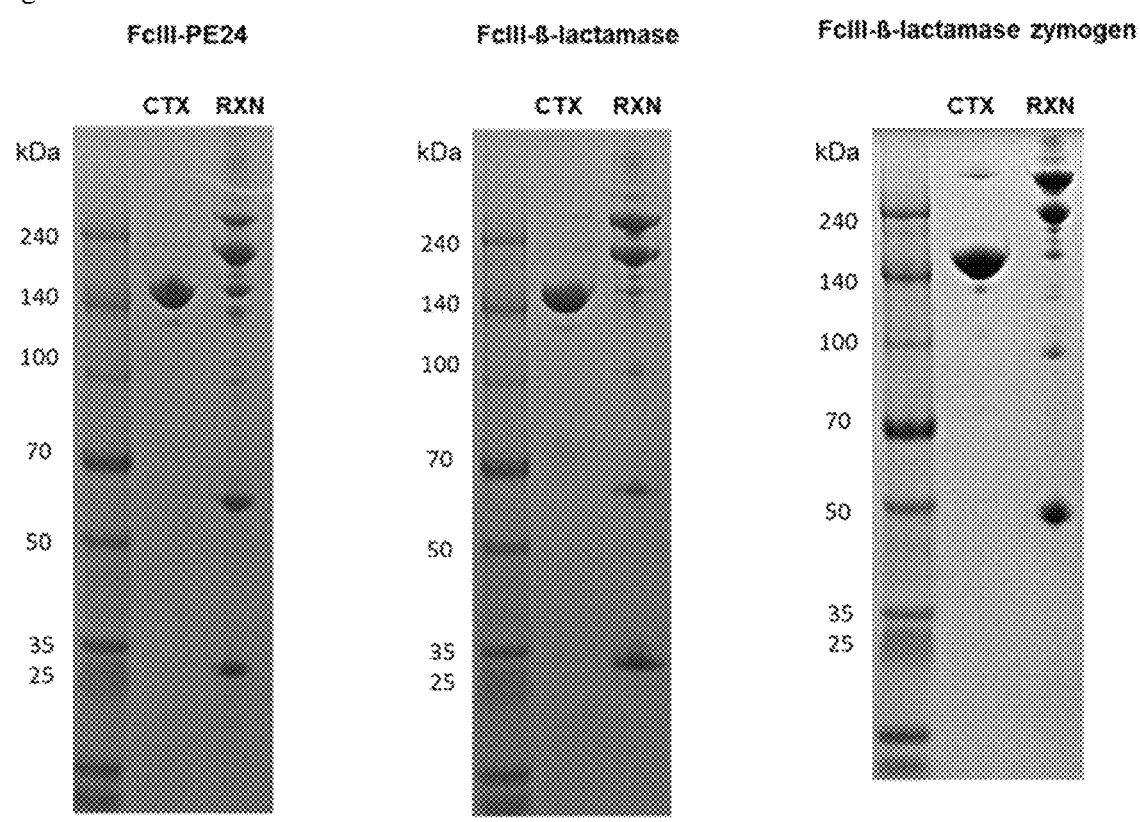
FIG. 7 illustrates the electrophoresis results of conjugating each of fusion proteins of the present invention and an antibody (cetuximab).

Example 4: Binding of Cetuximab and Substances Modified with Conjugating Peptides, and Separation and Activity of Conjugates Example 4-1: Confirmation of Binding of Cetuximab and Substance Modified with Conjugating Peptide To confirm binding of an antibody and each of substances modified with the conjugating peptides obtained according to Example 3 (FcIII-ß-lactamase, FcIII-ß-lactamase zymogen, and FcIII-PE24), cetuximab and each of substances modified with the conjugating peptides were mixed in a ratio of 1:5, and irradiated with ultraviolet light of 365 nm for 2 hours using a UV hand lamp (Lklab, U01-133-194) on a pH 7.4 1×PBS buffer. As a result, it was confirmed that cetuximab was bound to each of the substances modified with the conjugating peptides (FcIII-ß-lactamase, FcIII-ß-lactamase zymogen, and FcIII-PE24) (see FIG. 7).

To confirm whether each substance modified with the conjugating peptide accurately binds site-specifically to the CH$_2$—CH$_3$ domain interface of the antibody, 10 μM human IgG1 and 30 μM FcIII-ß-lactamase were mixed in a fixed concentration ratio, and the mixture was treated with Z-domain while increasing the concentration thereof from 10-35 μM at intervals of 5 μM, and subjected to photoreaction while irradiated with ultraviolet light of 365 nm for 2 hours using a UV hand lamp. The Z-domain binds to the same $CH_2$—$CH_3$ domain interface as that of the FcIII peptide.

Figure 8:
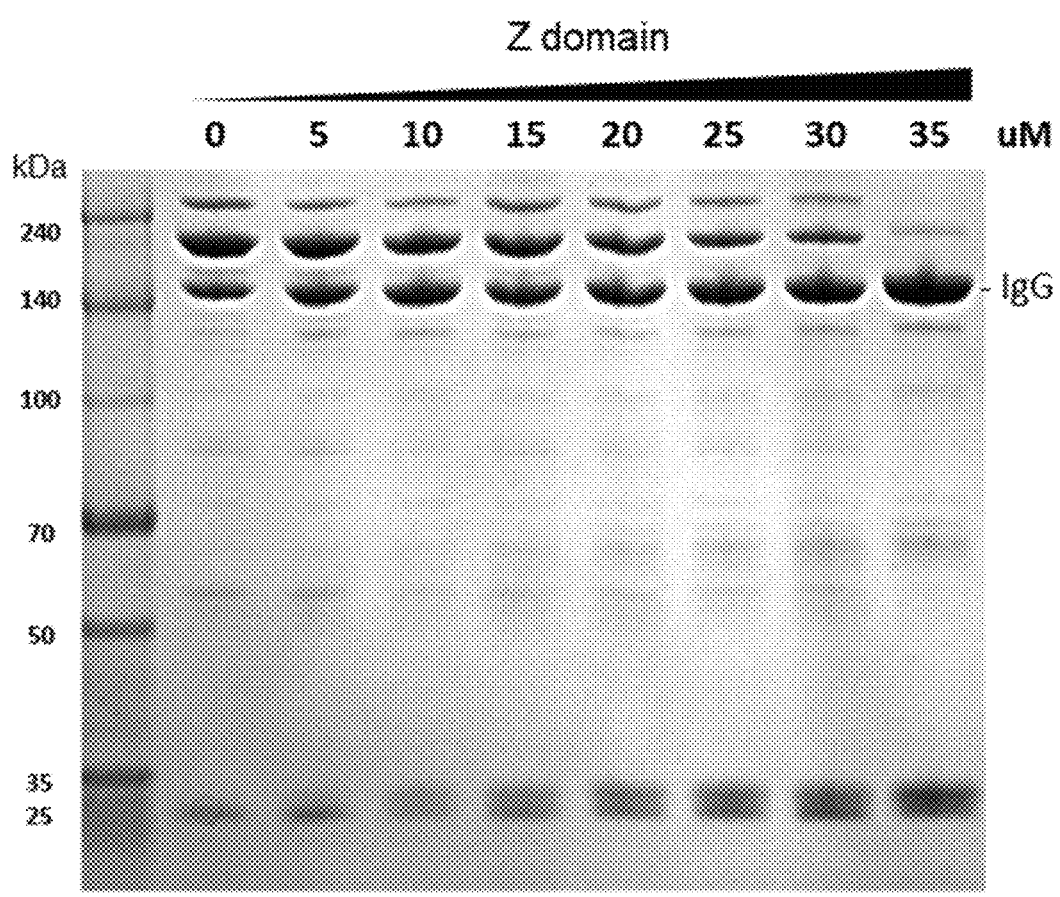
FIG. 8 illustrates the results of inhibition of Z-domain to conjugation between an antibody (cetuximab) and a fusion protein of the present invention, which demonstrates the site-specificity of the photoreaction.

As a result, it was confirmed that the formed human IgG1-FcIII-ß-lactamase was significantly reduced when photoreaction was performed after treatment with Z-domain at a concentration of 35 μM, which was higher than the concentration of FcIII-ß-lactamase. It is suggested indirectly that the FcIII fusion protein binds site-specifically to the Fc domain of the antibody (see FIG. 8).

Figure 9A:
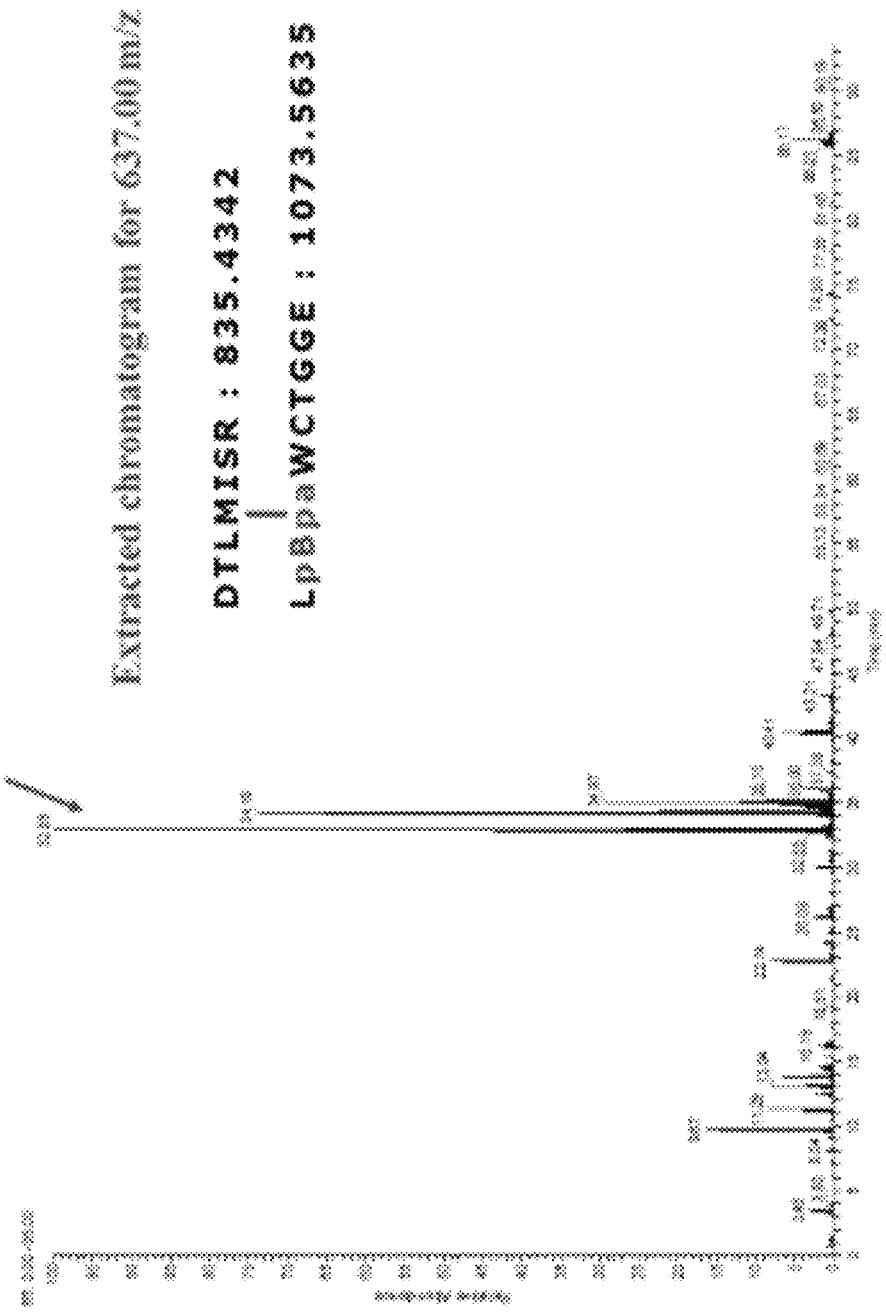
FIG. 9a-FIG. 9c illustrate the results of confirming, through LC-MS/MS, a site where the Fc conjugating peptide of the present invention and an antibody (cetuximab) were conjugated.
Figure 9B:
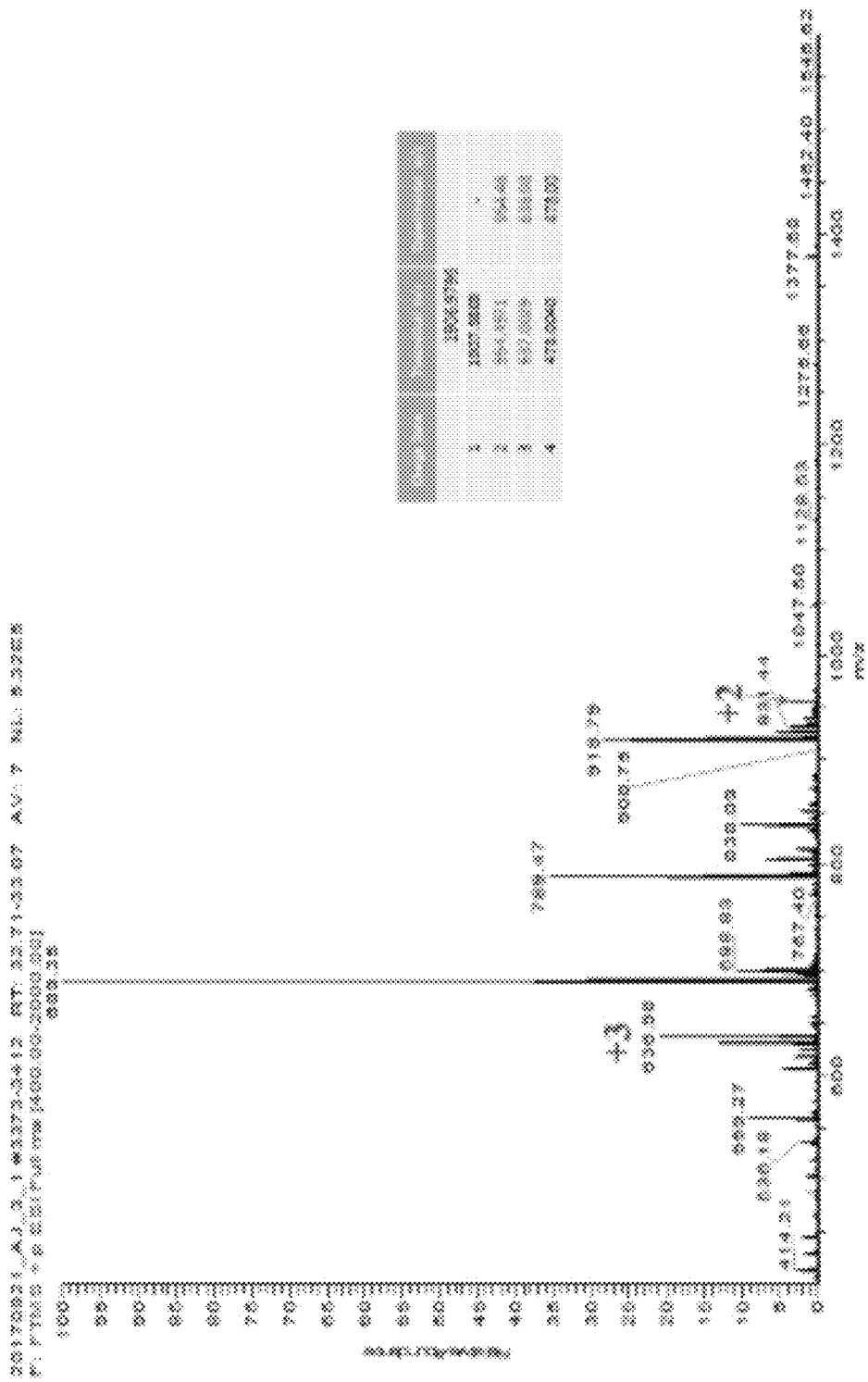
Figure 9C:
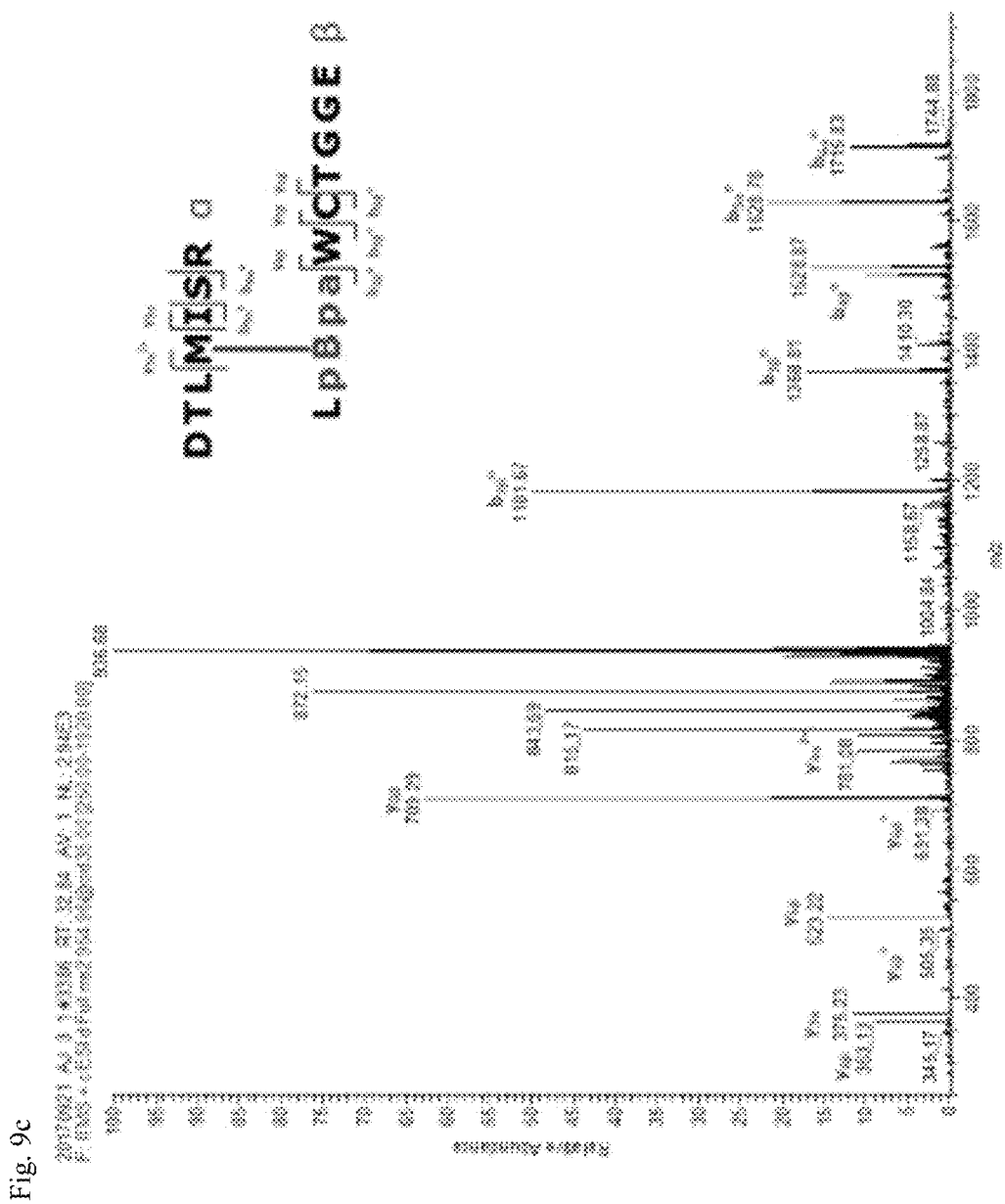

In addition, to confirm the conjugation position of the antibody and the substance modified with the conjugating peptide, analysis was performed using LC-MS/MS. The cetuximab-FcIII-ß-lactamase conjugate was subjected to trypsin/glutamyl endopeptidase mixture digestion and analyzed. As a result, the peaks of conjugate fragments generated site-specifically were confirmed due to the covalent bond formed between the functional group of pBpa inserted at position Val10 of FcIII and the functional group of Met252 of the antibody (see FIG. 9).

Example 4-2: Separation of Antibody-Biomolecule Conjugate in which Cetuximab and Substance Modified with Conjugated Peptide are Bound To separate an antibody-biomolecule conjugate in which a substance modified with one conjugated peptide is bound to the antibody, an antibody-biomolecule conjugate in which the antibody is bound to the substance modified with the conjugating peptide of Example 4 was mixed with 5 ml of 1×PBS (pH 7.4), and then 1 ml of a protein A 50% resin slurry (CaptivA Protein A resin, Repligen) was added thereto, followed by rotating at 4° C. for 1.5 hours. The reaction solution was loaded on an empty column, allowing the resin to be completely precipitated, and washing was performed by loading 30 ml of 1×PBS (pH 7.4). Thereafter, 5 ml of an elution buffer (pH 3.0 0.1 M glycine) was loaded to obtain a product, and 125 μl of a neutralization buffer (pH 9.0 Tris) was added for pH titration.

Figure 10:
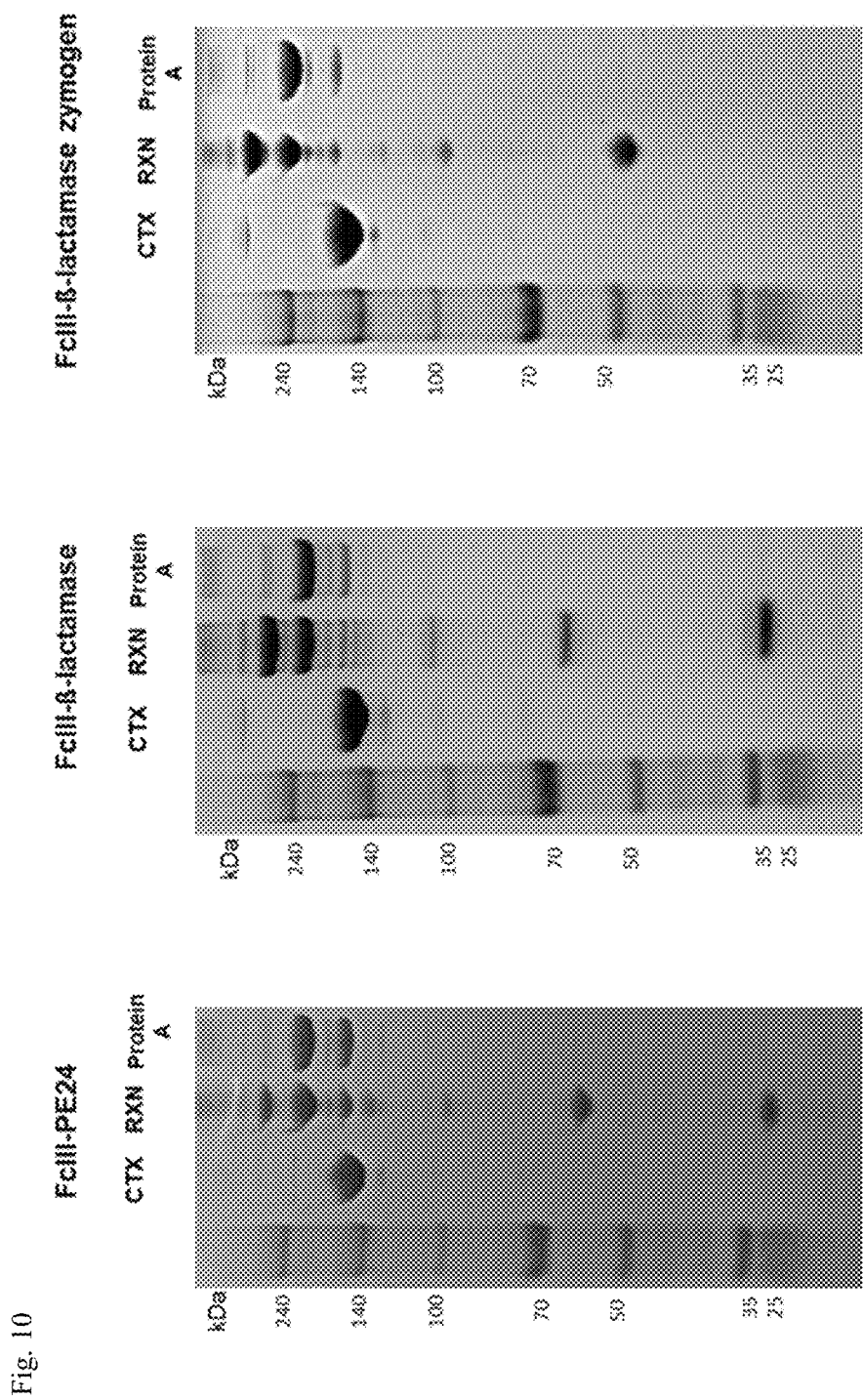
FIG. 10 illustrates the results of observing, through electrophoresis, isolation of a cetuximab-FcIII-PE24 conjugate in which the fusion protein of the present invention and an antibody (cetuximab) were conjugated at 1:1.

As a result, it was confirmed that the resulting product was a mixture of an unconjugated antibody and the antibody-biomolecule conjugate in which the substance modified with one conjugated peptide is bound to the antibody (see FIG. 10).

Example 4-3: Confirmation of EF2 Ribosylation Activity of Cetuximab-FcIII-PE24 Conjugate To measure the ADP-ribosylation activity of a cetuximab-FcIII-PE24 conjugate, ADP-ribose transition from biotinylated $MAD^+$ to EF-2 was measured using a method by Zhang and Snyder.

PE24 and the cetuximab-FcIII-PE24 conjugate were each diluted to 1 nM in 20 mM Tris-HCl (pH 7.4), 1 mM EDTA, and 1 mM DTT, respectively, and incubated with a wheat embryo extract in the presence of 50 nM biotinylated $NAD^+$ at 37° C. for 1 hour. Subsequently, the reaction was terminated with 5× sodium dodecyl sulfate (SDS) gel loading buffer. Proteins were separated on SDS-12% (w/v) polyacrylamide gel. Biotinylated EF-2 was detected by western blotting using a streptavidin-horseradish peroxidase (HRP) conjugate. Western blot images were analyzed using the ChemiDoc XRS system.

Figure 11:
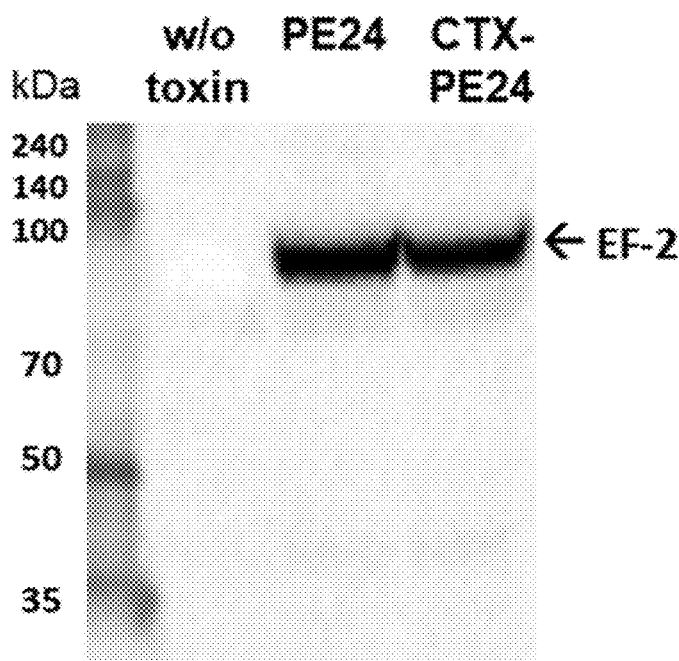
FIG. 11 illustrates the results of confirming the EF2 ribosylation activity of the cetuximab-FcIII-PE24 of the present invention.

As a result, it was confirmed that, like PE24, the cetuximab-FcIII-PE24 conjugate also inactivated EF-2 by ADP-ribosylation (see FIG. 11).

Example 4-4: Confirmation of Cell Growth Inhibitory Activity of Cetuximab-FcIII-PE24 Conjugate To confirm the activity of a cetuximab-FcIII-PE24 conjugate produced through photoreaction, cell viability assay was performed using a cell line overexpressing, on the cell surface, EGFR, which is a specific antigen to which cetuximab binds.

The EGFR cell line A431 (SIGMA Aldrich, 85090402) was cultured in a DMEM medium (10% FBS, streptomycin), and then seed-cultured on a 96-well plate at a density of $2 \times 10^3$ cells/well. After 24 hours, the cells were treated with cetuximab-FcIII-PE24 at concentrations of 0 nM, 0.016 nM, 0.16 nM, 1.6 nM, and 16 nM, and incubated at 37° C. and under the condition of 5% $CO_2$ for 72 hours. Thereafter, the cells were treated with 20 μl/well of an MTS solution (Promega, G3580), and after 2 hours, absorbance at 490 nm was measured.

Figure 12:
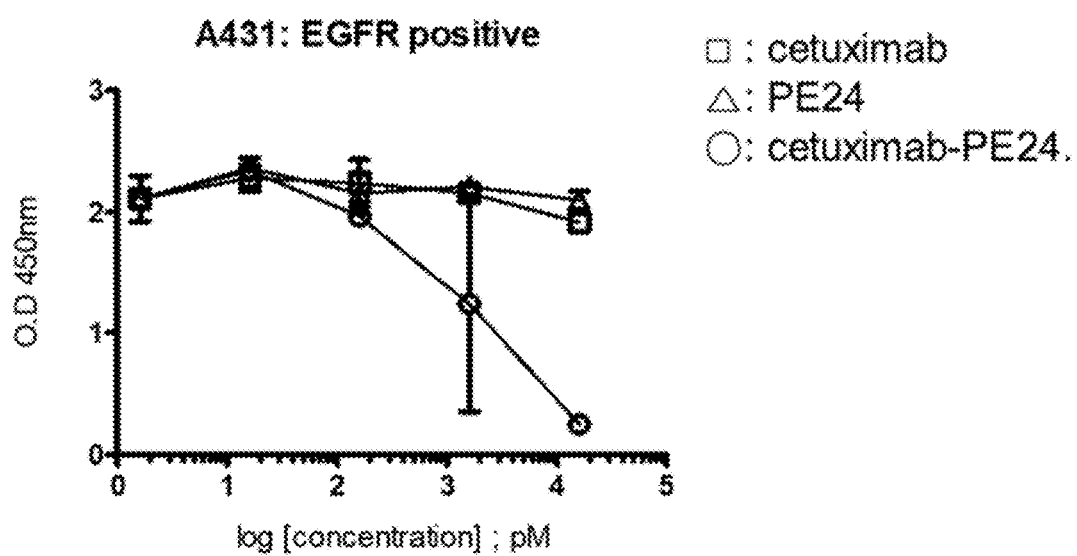
FIG. 12 illustrates the results of confirming the cell growth inhibitory activity of the cetuximab-FcIII-PE24 conjugate of the present invention.

As a result, it was confirmed that, the higher the concentration of cetuximab-FcIII-PE24 conjugate treated, the lower the absorbance, and cell viability was significantly reduced in the wells treated with the conjugate, compared to the wells treated with wild-type cetuximab and PE24 as negative controls (see FIG. 12).

Example 5: Binding of Trastuzumab and Substances Modified with Conjugating Peptides, and Separation and Activity of Conjugates

Example 5-1: Confirmation of Binding of Trastuzumab and FcIII-PE24

To confirm binding of an antibody and the substance modified with the conjugating peptide obtained according to Example 3 (FcIII-PE24), trastuzumab and PE24 modified with the conjugating peptide were mixed in a ratio of 1:5, and irradiated with ultraviolet light of 365 nm for 2 hours using a UV hand lamp (Lklab, U01-133-194) on a pH 7.4 1×PBS buffer. As a result, it was confirmed that trastuzumab and the substance modified with the conjugating peptide (FcIII-PE24) were bound (see FIG. 13).

Example 5-2: Separation of Trastuzumab-FcIII-PE24 Conjugate

To separate an antibody-biomolecule conjugate in which a substance modified with one conjugated peptide is bound to the antibody, an antibody-biomolecule conjugate in which the antibody is bound to the substance modified with the conjugating peptide of Example 4 was mixed with 5 ml of 1×PBS (pH 7.4), and then 1 ml of a protein A 50% resin slurry (CaptivA Protein A resin, Repligen) was added thereto, followed by rotating at 4° C. for 1.5 hours. The reaction solution was loaded on an empty column, allowing the resin to be completely precipitated, and washing was performed by loading 30 ml of 1×PBS (pH 7.4). Thereafter, 5 ml of an elution buffer (pH 3.0 0.1 M glycine) was loaded to obtain a product, and 125 μl of a neutralization buffer (pH 9.0 Tris) was added for pH titration.

Figure 13:
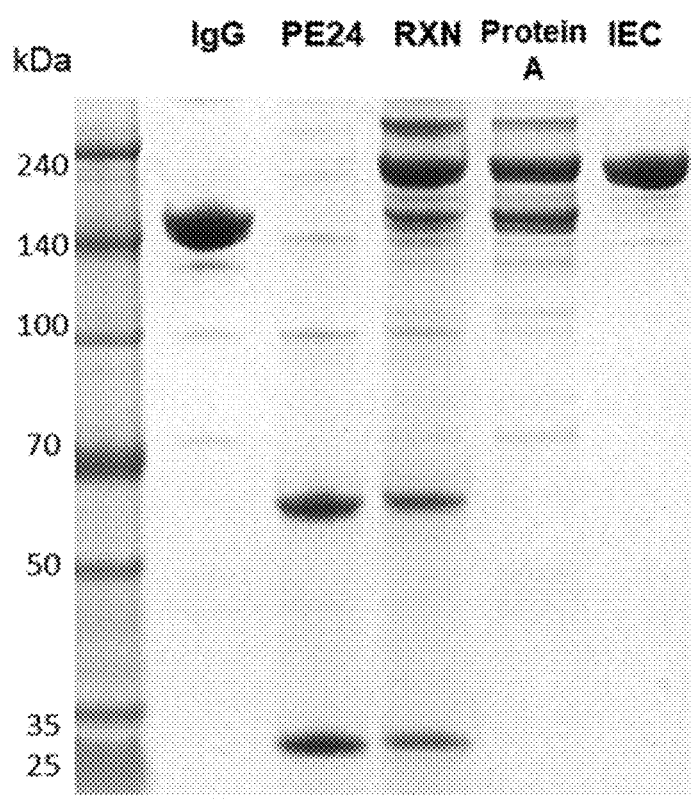
FIG. 13 illustrates the results of observing, by electrophoresis, site-specific conjugation between the fusion protein of the present invention and an antibody (trastuzumab) and isolation of a trastuzumab-FcIII-PE24 conjugate in which the fusion protein and the antibody were bound at 1:1.

As a result, it was confirmed that the resulting product was a mixture of an unconjugated antibody and the antibody-biomolecule conjugate in which the substance modified with one conjugated/peptide is bound to the antibody (see FIG. 13). The resulting product was mixed with a 20 mM phosphate buffer (pH 7.9), followed by continuous anion chromatography (mono-Q column, GE Healthcare Life Science, USA), thereby separating the unbound antibody and the form in which the substance modified with one conjugating peptide is bound to the antibody (see FIG. 13).

Example 5-3: Confirmation of Cell Growth Inhibitory Activity of Trastuzumab-FcIII-PE24 Conjugate To confirm the activity of a trastuzumab-FcIII-PE24 conjugate produced through photoreaction, cell viability assay was performed using cell lines overexpressing HER2, which is a specific antigen to which trastuzumab binds, and cell lines that do not express HER2.

HER2-overexpressing cell lines BT-474 (Korean Cell Line Bank, 60062), HCC-1954 (Korean Cell Line Bank, 9S1954), and MDA-MB-453 (Korean Cell Line Bank, 30131), and HER2 non-expressing cell line MDA-MB-231 (Korean Cell Line Bank, 30026) were cultured in RPMI media (10% FBS, streptomycin), and then seed-cultured in a 96-well plate at a density of $3-5\times10^3$ cells/well. After 24 hours, the cell lines were treated with trastuzumab-FcIII-PE24 at concentrations of 0 nM, 0.0064 nM, 0.032 nM, 0.16 nM, 0.8 nM, 4 nM, and 20 nM, and incubated at 37° C. and under the condition of 5% $CO_2$ for 72 hours. Thereafter, the cell lines were treated with 10 µl/well of a WST-8 solution (Dojindo, CK04-11), and after 2 hours, absorbance at 450 nm was measured.

Figure 14:
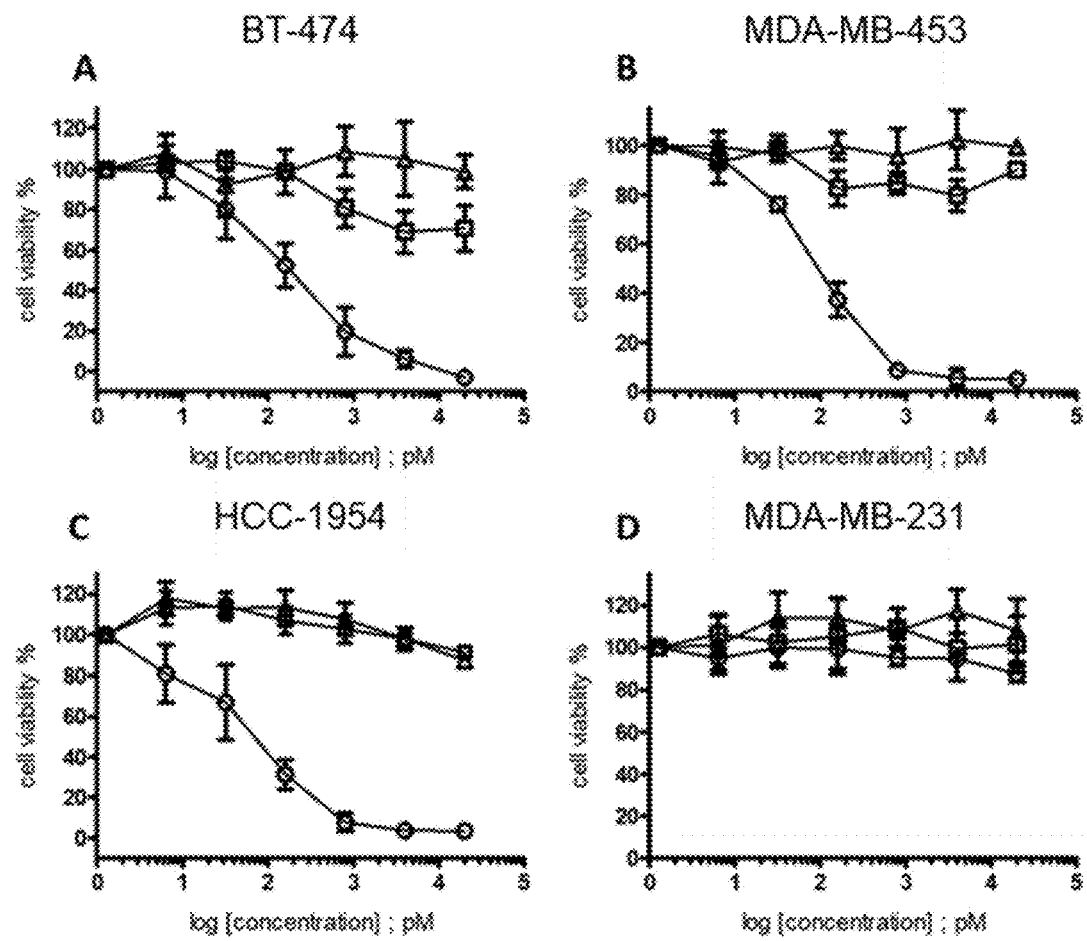
FIG. 14 illustrates the results of confirming the cell growth inhibitory activity of the trastuzumab-FcIII-PE24 conjugate of the present invention.

As a result, it was confirmed that, the higher the concentration of trastuzumab-FcIII-PE24 conjugate treated on the HER2-overexpressing cells, the lower the absorbance, and cell viability was significantly reduced in the wells treated with the conjugate, compared to the wells treated with wild-type trastuzumab and PE24 as negative controls. In contrast, it was confirmed that the cytotoxicity of the trastuzumab-FcIII-PE24 conjugate did not act on the HER2 non-expressing cells within the corresponding concentration range (see FIG. 14).

INDUSTRIAL APPLICABILITY

According to the present invention, by preparing a substance modified with the Fc site-specific conjugating peptide in which a specific position is substituted with a photoreactive functional group, and then conjugating an antibody to the substance through photoreaction, the substance can be linked site-specifically to the antibody with a high efficiency through simple photoreaction. Accordingly, the substance can be used for the production of antibody conjugates in which various types of substances and antibodies are linked, and commercialization thereof can be accelerated.

While specific embodiments of the present invention have been described in detail, it will be obvious to those of ordinary skill in the art that these detailed descriptions are merely exemplary embodiments and should not be construed as limiting the scope of the present invention. Therefore, the substantial scope of the present invention should be defined by the appended claims and equivalents thereof.

SEQUENCE LIST FREE TEXT

Electronic files attached.

The invention claimed is:

1. An Fc site-specific conjugating peptide mutant comprising the amino acid sequence of SEQ ID NO: 1, wherein the amino acid sequence of the Fc site-specific conjugating peptide further comprises a valine to p-benzoyl phenylalanine substitution at position 10, and wherein the Fc site-specific conjugating peptide mutant comprising p-benzoyl phenylalanine substitution at position 10 shows higher binding efficiency to Fc site of an antibody than a mutant comprising p-benzoyl phenylalanine substitution at position 5 or 11.

* * * * *